(12) United States Patent
Kansal et al.

(10) Patent No.: US 8,084,630 B2
(45) Date of Patent: Dec. 27, 2011

(54) PROCESS FOR THE SYNTHESIS OF RAMELTEON AND ITS INTERMEDIATES

(75) Inventors: Vinod Kumar Kansal, Haryana (IN); Dhirenkumar N. Mistry, Gujarat (IN); Sanjay L. Vasoya, Gujarat (IN); Michal Rafilovich, Petach-Tikva (IL); Elena Ben Moha-Lerman, Kiryat Ono (IL); Revital Lifshitz-Liron, Hertzlia (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 797 days.

(21) Appl. No.: 12/131,901

(22) Filed: Jun. 2, 2008

(65) Prior Publication Data

US 2009/0069581 A1    Mar. 12, 2009

Related U.S. Application Data

(60) Provisional application No. 60/932,804, filed on May 31, 2007, provisional application No. 61/001,610, filed on Nov. 1, 2007, provisional application No. 61/047,623, filed on Apr. 24, 2008.

(51) Int. Cl.
  *C07D 307/77* (2006.01)
  *C07D 307/79* (2006.01)
(52) U.S. Cl. ........................................ 549/458; 549/462
(58) Field of Classification Search .................. 549/458, 549/462
  See application file for complete search history.

(56) References Cited

U.S. PATENT DOCUMENTS

| | | | |
|---|---|---|---|
| 4,943,635 A | 7/1990 | Corey et al. | |
| 5,552,548 A | 9/1996 | Quallich | |
| 5,719,186 A | 2/1998 | Cooper et al. | |
| 6,034,239 A | 3/2000 | Ohkawa et al. | |
| 6,333,198 B1 | 12/2001 | Edmeades et al. | |
| 2009/0082432 A1 | 3/2009 | Czarnik | |

FOREIGN PATENT DOCUMENTS

| | | |
|---|---|---|
| EP | 0 885 210 | 12/1998 |
| EP | 1 792 899 | 6/2007 |
| JP | 11080106 | 3/1999 |
| JP | 11140073 | 5/1999 |
| JP | 2002/253297 | 9/2002 |
| WO | WO 99/63977 | 12/1999 |
| WO | WO 02/16337 | 2/2002 |
| WO | 2006/030739 A1 | 3/2006 |
| WO | 2006/055187 A1 | 5/2006 |
| WO | WO 2008/062468 | 5/2008 |
| WO | WO 2008/123067 | 10/2008 |
| WO | WO 2008/150953 | 12/2008 |
| WO | WO 2008/151170 | 12/2008 |
| WO | WO 2009/056993 | 5/2009 |
| WO | WO 2009/084023 | 7/2009 |
| WO | WO 2009/106966 | 9/2009 |
| WO | WO 2010/007022 | 1/2010 |

OTHER PUBLICATIONS

Fukatsu, et al. "Synthesis of a Novel Series of Benzocycloalkene Derivatives as Melatonin Receptor Agonists", J. Med. Chem., 45: 4212-4221 (2002).
"Ramelteon", Drug of the future 28(10): 950-958 (2003).
Romo et al, "Total Synthesis and Immunosuppressive Activity of (-)-Pateamine A and Related Compounds; Implementaion of a B-Lactam-Based Macrocyclization", Journal Am. Chem. Soc. vol. 120, No. 47, 12237-12254 (1998).
Snyder et al., *Introduction to Modern Liquid Chromatography*, 2$^{nd}$ ed. (John Wiley & Sons: New York 1979).
Tarui, et al., "Kinetic Resolution of an Indan Derivative Using *Bacillus* sp. SUI-12: Synthesis of a Key Intermediate of the Melatonin Receptor Agonist TAK-375," Journal of Bioscience & Bioengineering. 93(1) 44-47 (2001).
Uchikawa et al, "Synthesis of a Novel Series of Tricyclic Indan Derivatives as Melatonin Receptor Agonists", J. Med. Chem. 45, 4222-4239 (2002).
Vakhlu et al., "Yeast Lipases: Enzyme Purification, biochemical Properties and Gene Cloning", Electronic Journal of Biotechnology, 2006, vol. 9, No. 1, p. 69-85.
Yamano et al, "Approach to the Stereoselective Synthesis of Melatonin Receptor Agonist Ramelteon via Asymmetric Hydrogenation", Tetrahedron Asymmetry, vol. 17, No. 2, 184-190 (2006).
"Intermediates of (S)-N-[2-(1, 6, 7, 8-tetrahydro-2H-indeno-[5, 4-b] furan-8-yl)ethyl] propionamide ((S)-N-[2-(1, 6, 7, 8-tetrahydro-2H-indeno-[5, 4-b] furan-8-yl)ethyl] propionamide", IPCOM000170556D, May 19, 2008.
Strobel, H.A.; Heineman, W.R., Chemical Instrumentation: A Systematic Approach, 3rd ed. (Wiley & Sons: New York 1989).
Greene, et al., "Asymmetric Hydrogenation of 3-oxo Carboxylates Using Binap-rhthenium Complexes: (R)-(-)-Methyl 3-Hydroxybutanoate", Organic Syntheses, Coll. vol. 9, p. 589-596 (1998).
Yamashita, et al., "Synthesis of Melatonin Receptor Agonist Ramelteon via Rh-catalyzed Asymmetric Hydrogenation of an Allylamine", Chemistry Letters, 38(1) 100-101 (2009).
S.M. Ray et al., "Investigation on Synthesis, hypotensive activity and highly selective adrenergic antagonistic activity of some simple and substituted indan derivatives" Journal of the Indian Chemical Society, 68(10):549-55 (1991).
International Search Report of Jul. 7, 2008 (Received in International Application No. PCT/US2008/002607).

*Primary Examiner* — Bernard Dentz
(74) *Attorney, Agent, or Firm* — Kenyon & Kenyon LLP

(57) ABSTRACT

The present invention provides processes and intermediates for the synthesis of ramelteon.

31 Claims, 1 Drawing Sheet

PROCESS FOR THE SYNTHESIS OF RAMELTEON AND ITS INTERMEDIATES

RELATED APPLICATIONS

This application claims priority of U.S. provisional patent application Nos. 60/932,804, filed May 31, 2007; 61/001,610, filed Nov. 1, 2007; and 61/047,623, filed Apr. 24, 2008. The entire contents of these applications are incorporated herein by reference.

FIELD OF THE INVENTION

The present invention relates to novel synthesis of (S)—N-[2-(1,6,7,8-tetrahydro-2H-indeno-[5,4-b]furan-8-yl)ethyl]propionamide, i.e. ramelteon.

BACKGROUND OF THE INVENTION

Ramelteon is a melatonin receptor agonist with both high affinity for melatonin MT1 and MT2 receptors and selectivity over the MT3 receptor. The empirical formula for ramelteon is $C_{16}H_{21}NO_2$, and its molecular weight is 259.34. Ramelteon is freely soluble in methanol, ethanol, DMSO, and 1-octanol, and highly soluble in water and aqueous buffer. Ramelteon has the following chemical structure:

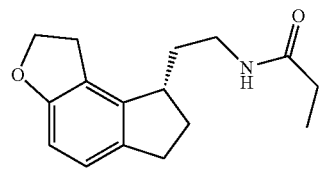

Ramelteon is the active ingredient in trademarked ROZEREM®, and is approved by the United States Food and Drug Administration for the treatment of insomnia characterized by difficulty with sleep onset.

Different processes for preparing (S)—N-[2-(1,6,7,8-tetrahydro-2H-indeno-[5,4-b]furan-8-yl)ethyl]propionamide, i.e. ramelteon, are disclosed in U.S. Pat. No. 6,034,239, JP 11080106, JP 11140073 and WO 2006/030739.

U.S. Pat. No. 6,034,239 describes the following processes for the preparation of ramelteon:

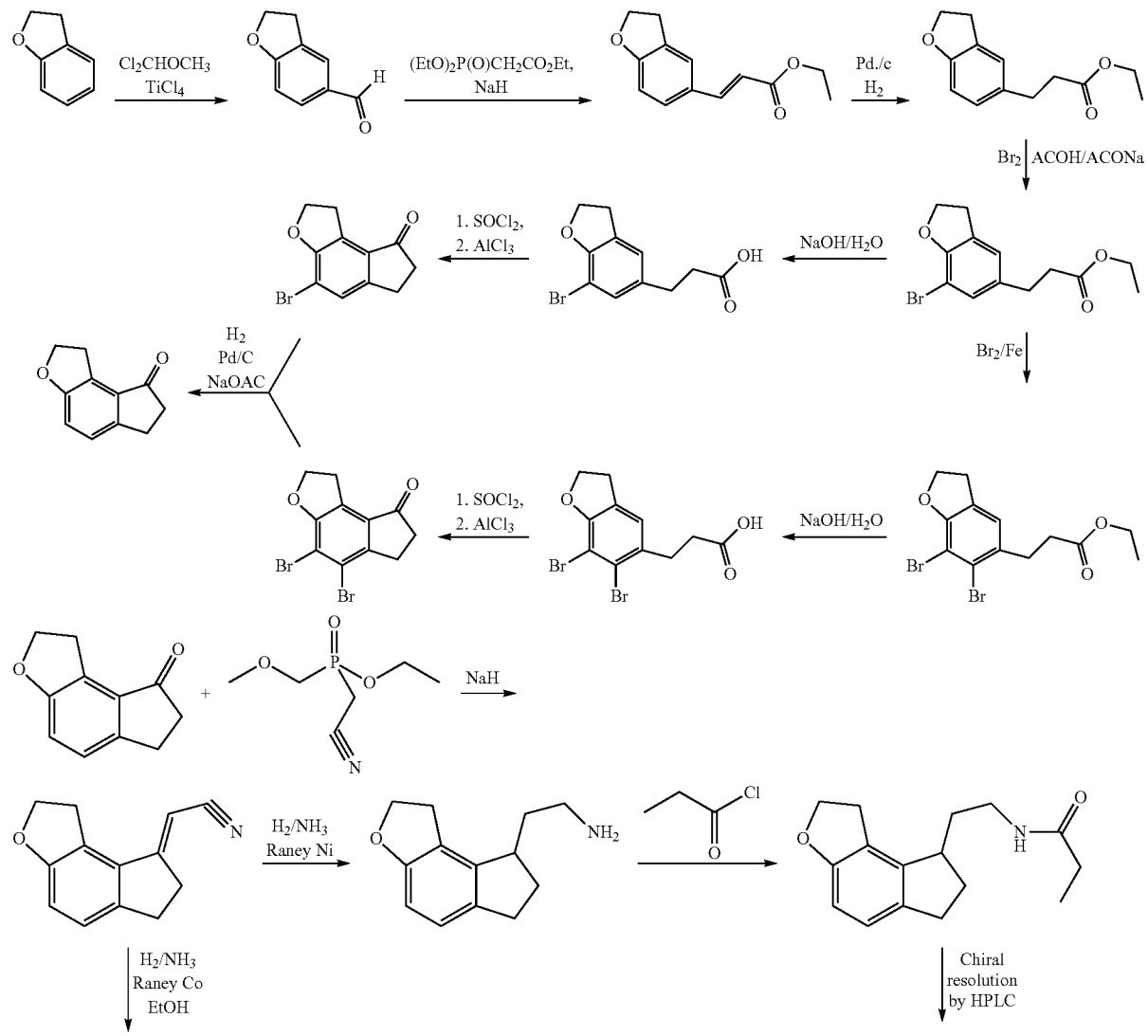

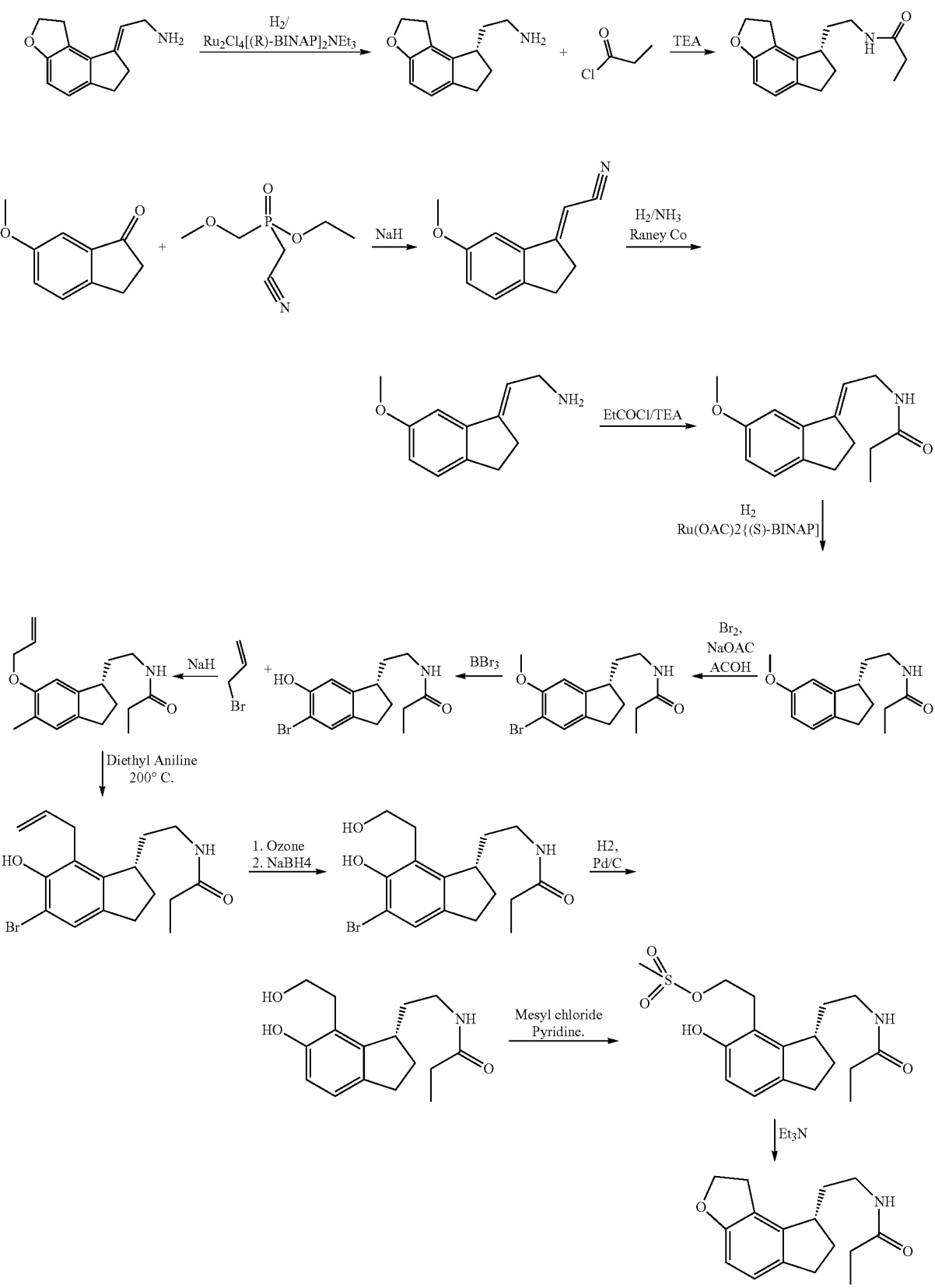

Japan Patent Publication No. 11080106 reports the following process for the preparation of ramelteon:
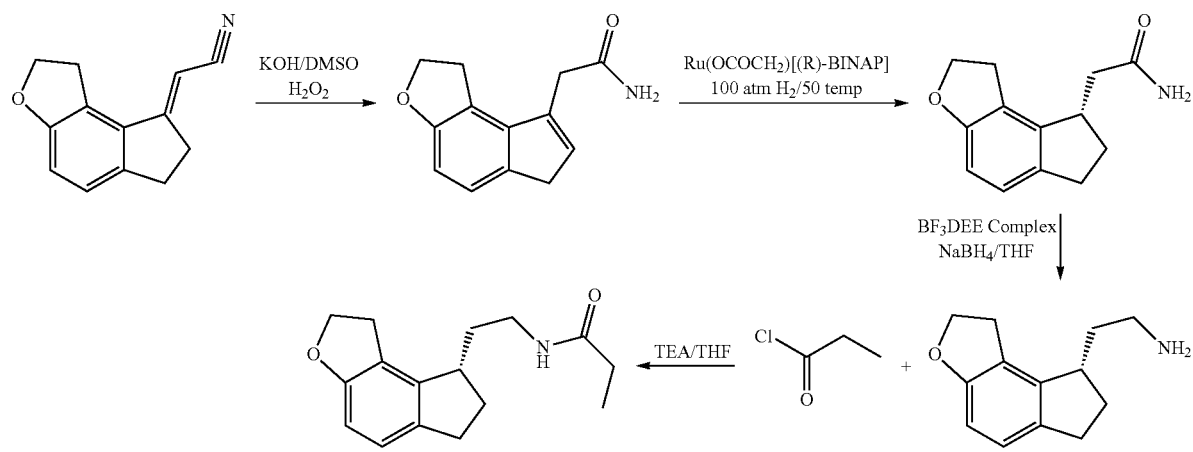
Japan Patent Publication no. 11140073 reports the following process for the preparation of an intermediate of ramelteon:
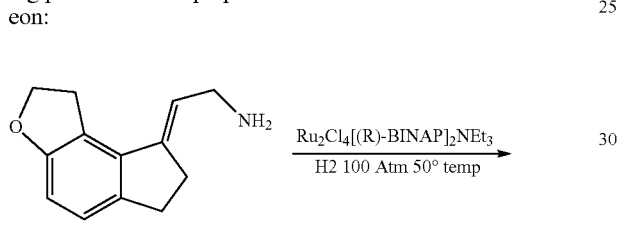
PCT Publication No. WO/2006/030739 reports the following process for the preparation of ramelteon:
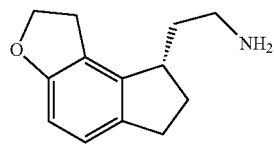
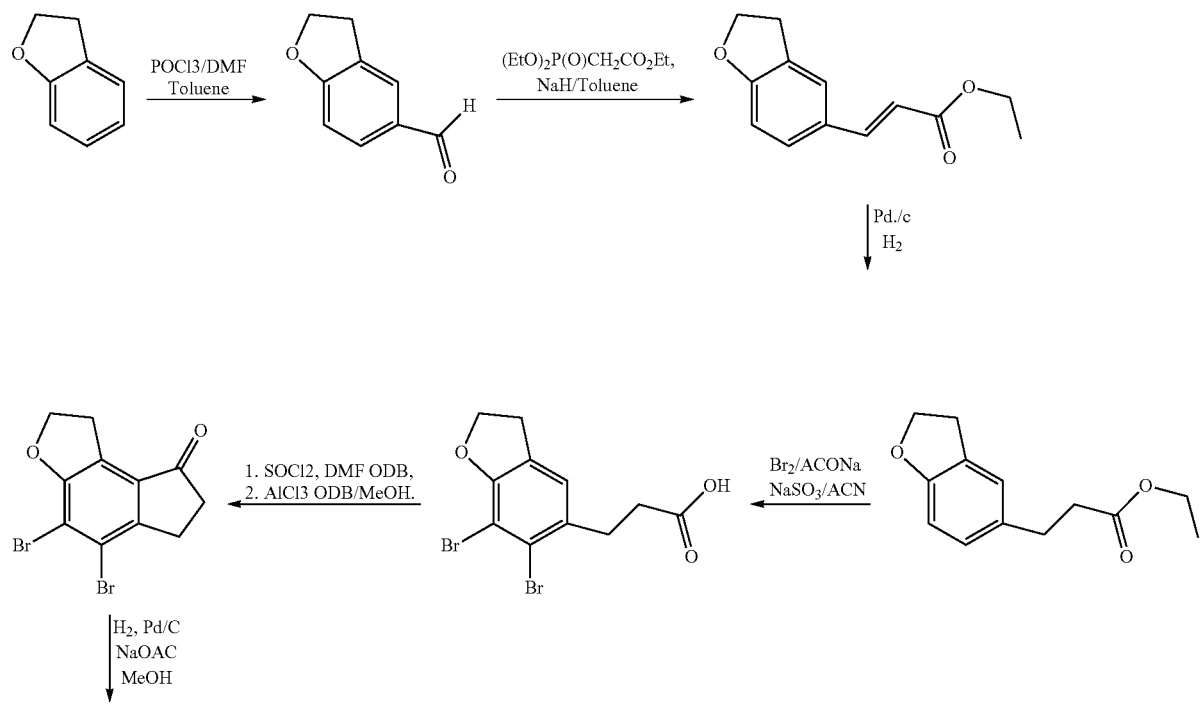

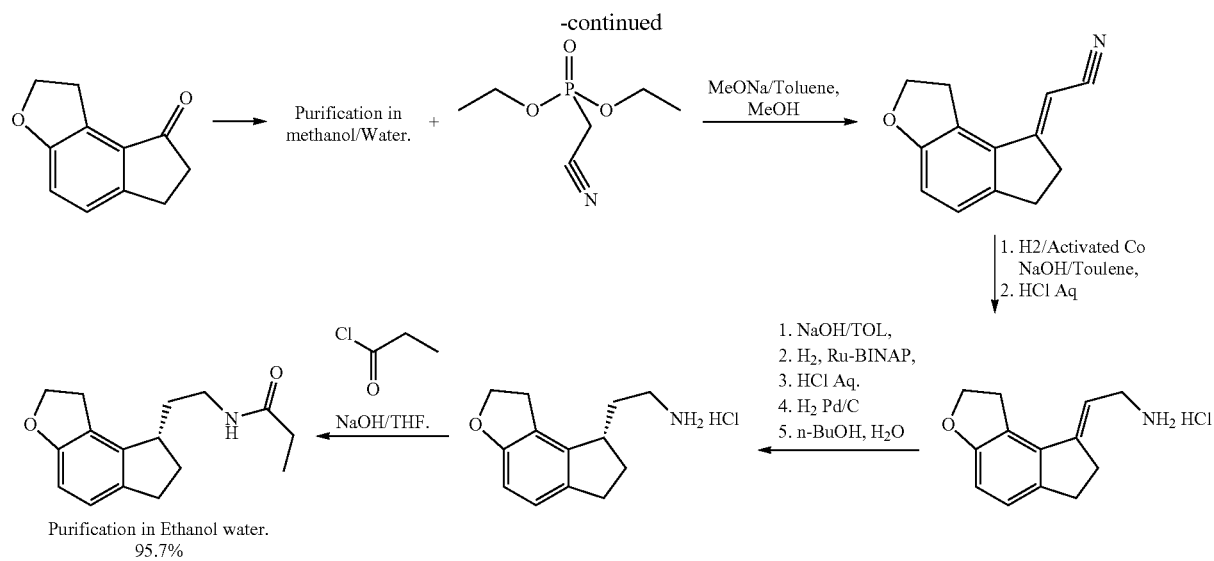
There is a pressing need in the art for new processes for the preparation of ramelteon suitable for industrial scale.
SUMMARY OF THE INVENTION
The present invention provides a method of preparing ramelteon which proceeds essentially as shown in Scheme 1:
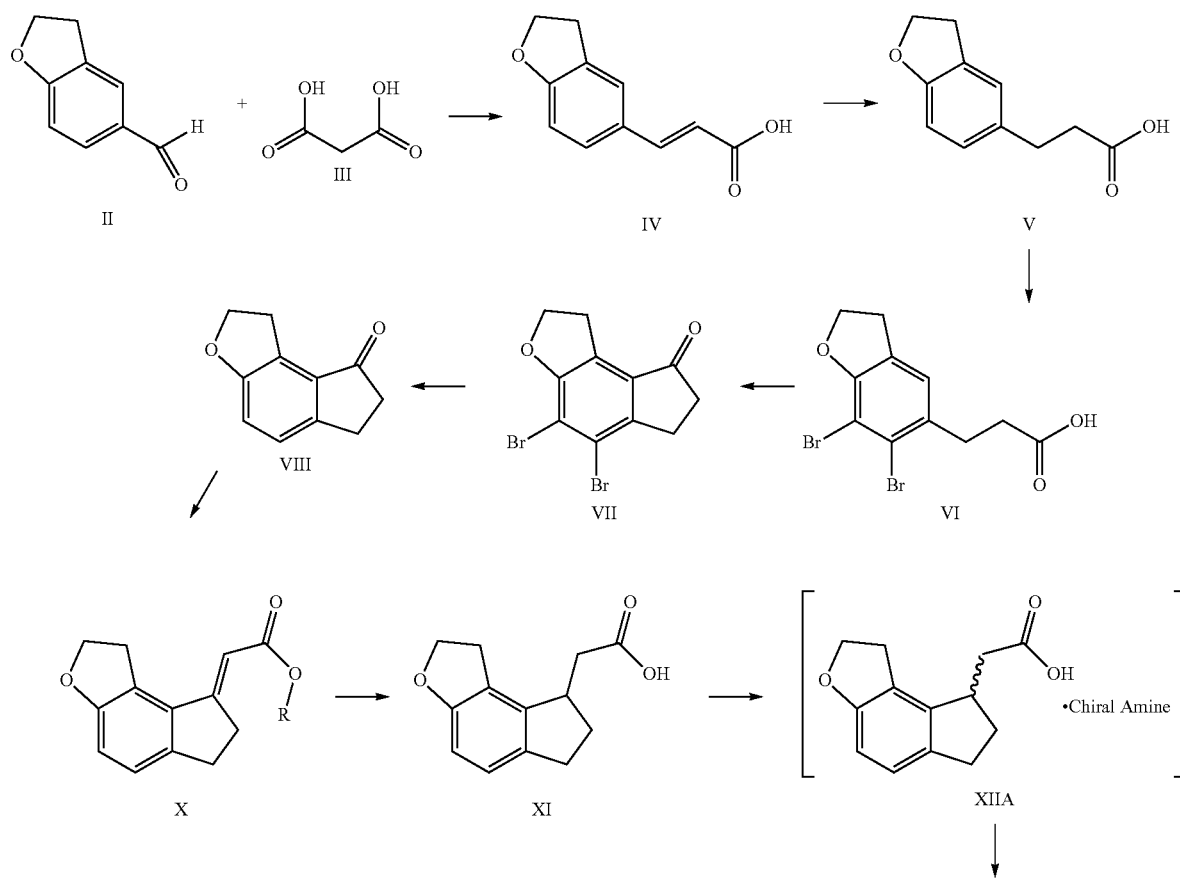

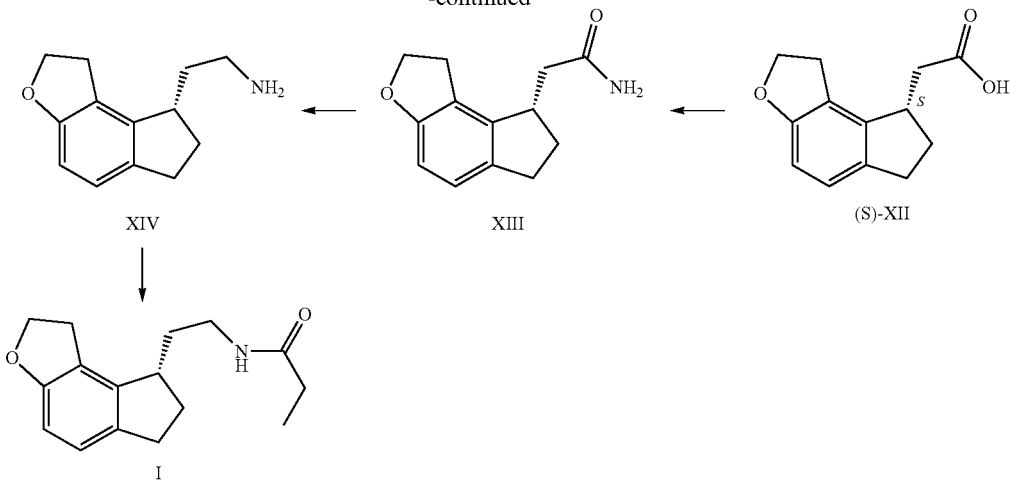

In one embodiment, the present invention provides a process for producing ramelteon intermediate of formula IV, comprising reacting the compound of Formula II with malonic acid III:

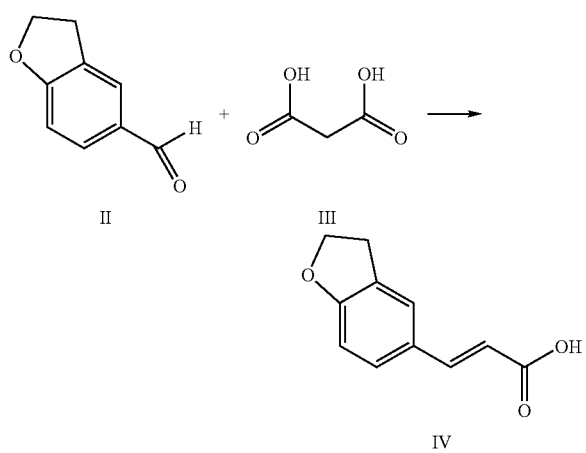

In one embodiment, the present invention encompasses a process for preparing ramelteon, by preparing the compound of Formula IV as described above, and converting it to ramelteon.

In another embodiment, the present invention encompasses a process for preparing a ramelteon intermediate of formula V, comprising reduction of compound of formula IV.

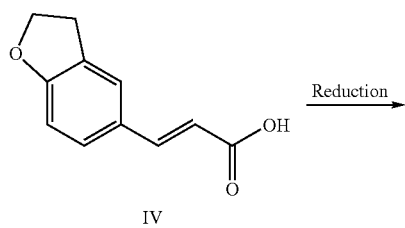

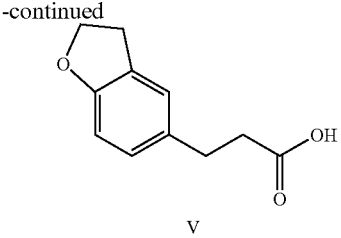

In one embodiment, the present invention encompasses a process for preparing ramelteon, by preparing the compound of Formula V as described above, and converting it to ramelteon.

The intermediate of formula VI may be prepared by reacting the compound of formula V with a halogenation agent such as bromine:

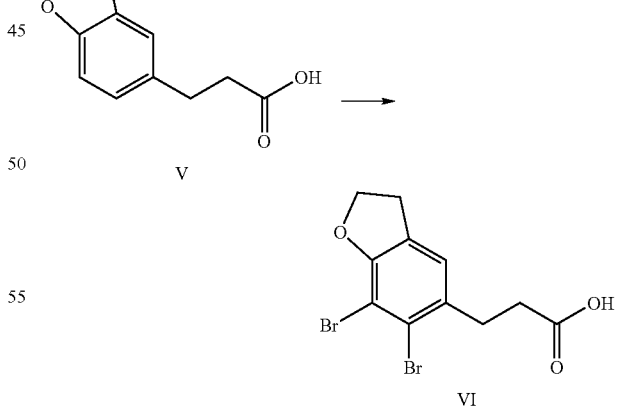

In one embodiment, the present invention encompasses a process for preparing ramelteon, by preparing the compound of Formula VI as described above, and converting it to ramelteon.

The compound of formula VI may then be cyclized to provide the compound of formula VII:

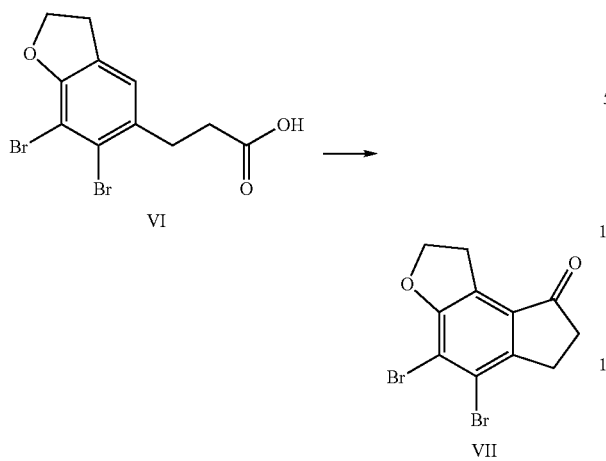

VI

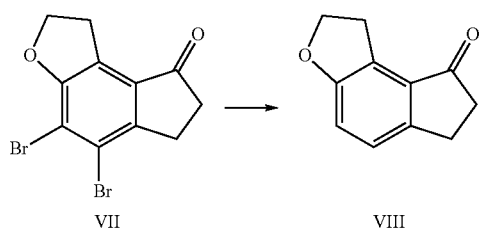

Reductive dehalogenation of the compound of formula VII may then be employed to generate the compound of structure VIII:

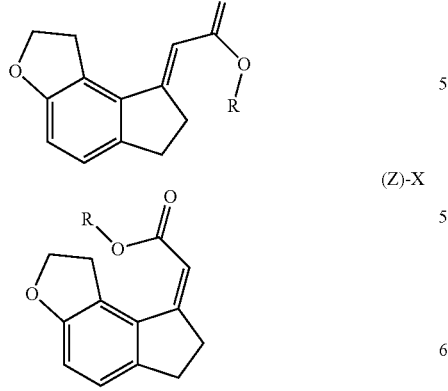

In one embodiment, the present invention encompasses a process for preparing ramelteon, by preparing the compound of Formula VIII as described above, and converting it to ramelteon.

In one embodiment, the present invention provides an intermediate having the structure X, the corresponding Z-isomer having the structure (z)-X, and mixtures thereof.

In X and (Z)-X, R is $C_1$ to $C_6$ straight or branched alkyl, $C_6$ to $C_{10}$ aryl, and $C_7$ to $C_{12}$ arylalkyl. Preferably, R is $C_1$ to $C_4$ straight or branched alkyl, phenyl or benzyl. More preferably, R is methyl or ethyl.

In one embodiment, the present invention provides a process for producing ramelteon intermediate of formula X, comprising the step of condensing the compound of Formula VIII with compound of formula IX in the presence of a base and an organic solvent.

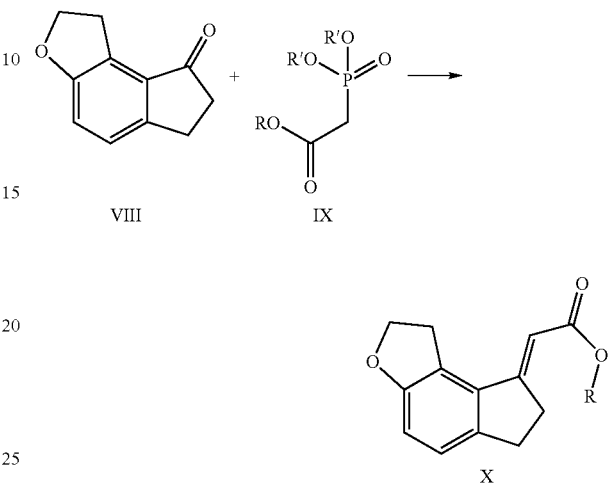

In the scheme above, R and R' are independently $C_1$ to $C_6$ straight or branched alkyl, $C_6$ to $C_{10}$ aryl, and $C_7$ to $C_{12}$ arylalkyl. Preferably, R and R' are independently $C_1$ to $C_4$ straight or branched alkyl, phenyl or benzyl. More preferably, R and R' are the same, and are methyl or ethyl.

In one embodiment, the present invention encompasses a novel process for preparing ramelteon, by preparing the compound of Formula X as described above, and converting it to ramelteon.

In one embodiment, the present invention provides a compound of Formula Xa:

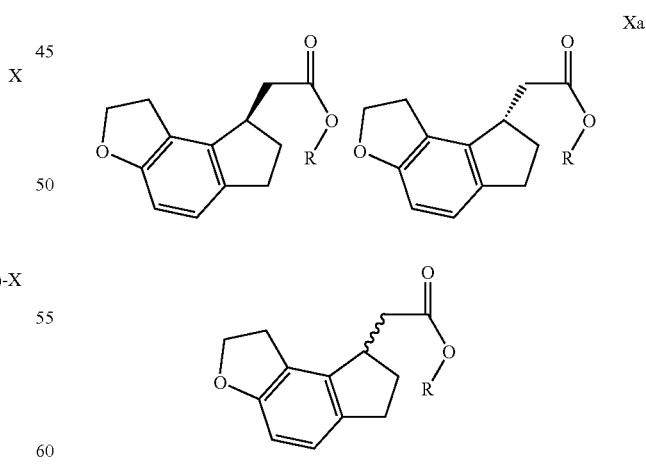

wherein R is as defined above. The compound Xa may be racemic, an isolated (R) or (S) enantiomer, or an enantiomerically enriched mixture thereof.

In another embodiment, the present invention provides a compound having the Formula XI:

XI

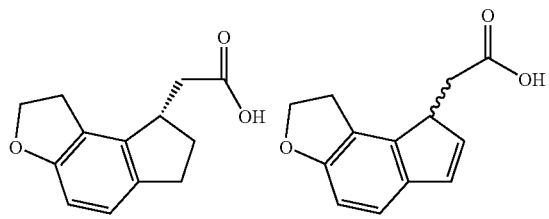

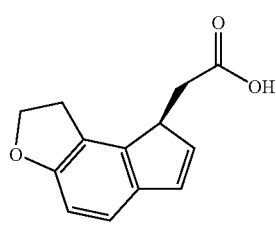

wherein XI may be racemic, an isolated (R) or (S) enantiomer, or an enantiomerically enriched mixture thereof.

In another embodiment, the present invention encompasses a process for preparing the ramelteon intermediate of formula XI, comprising hydrolysis of compound of formula X, followed by reduction of the double bond.

In another alternative embodiment, the present invention encompasses a novel process for preparing the racemic ramelteon intermediate of formula XI, comprising reduction of compound of formula X, wherein R is as defined above, followed by hydrolysis.

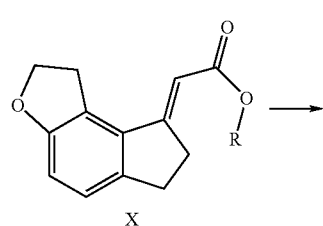

X

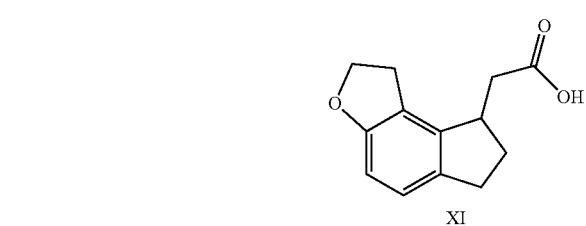

XI

In one embodiment, the present invention encompasses a novel process for preparing ramelteon, by preparing the compound of Formula XI as described above, and converting it to ramelteon.

In one embodiment, the present invention provides a compound of Formula XII, including the individual isomers and non-racemic mixture thereof:

XII

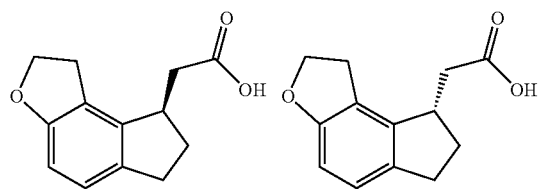

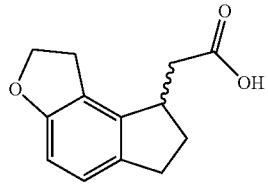

and further provides chiral amine salts thereof, represented by formula XIIa:

XIIa

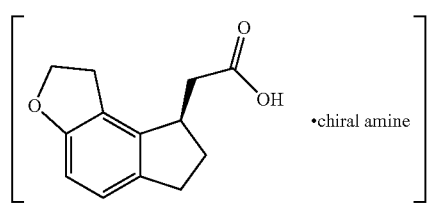

XIIa

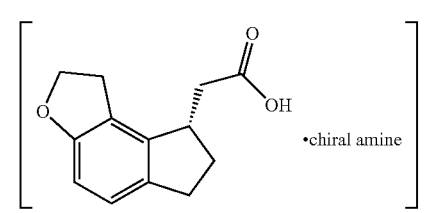

In another embodiment, the present invention encompasses a process for preparing the ramelteon intermediate enantiomer of formula (S)-XII, comprising resolution of the racemic form of compound of formula XI by diastereomeric crystallization with an organic chiral amine and acidifying. The isolated compound (S)-XII preferably has an enantiomeric excess over the racemate XII of at least about 75%, at least about 90%, more preferably at least about 98%, and most preferably exhibits an enantiomeric excess of about 99%, and in one embodiment about 90% to about 100%. The chemical purity can be at least about 50%, more preferably at least about 75%, and in one embodiment about 90% to about 100% as measured by HPLC.

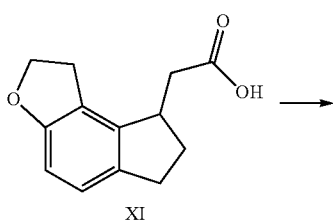

XI

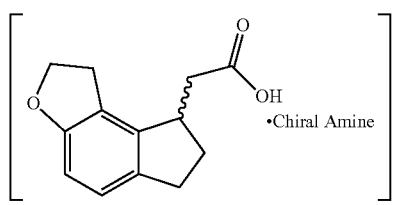

XIIa

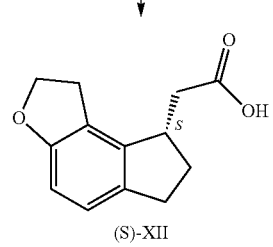

(S)-XII

In one embodiment, the present invention provides a compound of formula (S)-XII.

In one embodiment, the present invention provides solid compound of formula (S)-XII.

In one embodiment, the present invention provides crystalline compound (S)-XII.

Crystalline compound (S)-XII Form I is characterized by a powder X-ray diffraction pattern with peaks at about 11.3, 15.3, 18.5, 22.0 and 24.3±0.2 degrees 2 theta. Compound (S)-XII crystalline Form I may be further characterized by a PXRD pattern substantially as depicted in FIG. 1. It will be understood that the expression "substantially as depicted" means that, as is well-known in the art, variations in a spectrum due to variables in sample condition, sample preparation, and measuring apparatus, inter alia, are to be taken into consideration when assessing the identity of two compounds based on their PXRD patterns.

In one embodiment, the present invention encompasses a process for preparing ramelteon, by preparing the compound of Formula (S)-XII as described above, and converting it to ramelteon.

In another embodiment, the present invention encompasses a process for preparing a ramelteon intermediate of formula XIII, comprising converting the —COOH group to form an activated acid derivative, followed by ammoniolysis of the activated acid derivative.

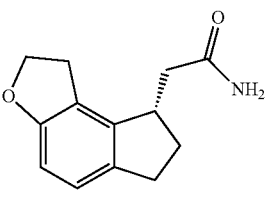

XIII

In another embodiment, the present invention encompasses an alternate process for preparing a ramelteon intermediate of formula XIII, comprising converting the —COOH group to compound of formula XII B, followed by the ammonolysis of the activated acid derivative.

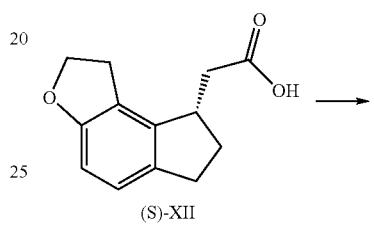

(S)-XII

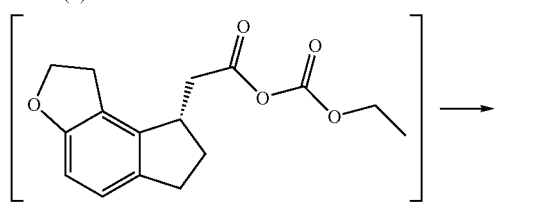

XII B

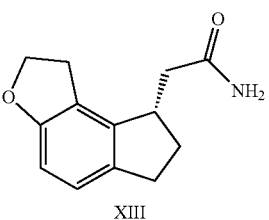

XIII

In one embodiment, the present invention encompasses a process for preparing ramelteon, by preparing the compound of Formula XIII using any of the processes described above, and converting it to ramelteon.

In another embodiment, the present invention encompasses an improved process for preparing a ramelteon intermediate of formula XIV, comprising reduction of compound of formula XIII with an amide reducing agent in an organic solvent. The compound of formula XIV may be purified via formation of a salt of formula XIVa.

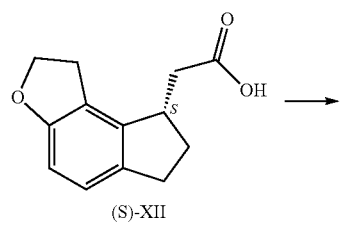

(S)-XII

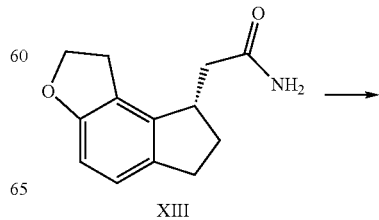

XIII

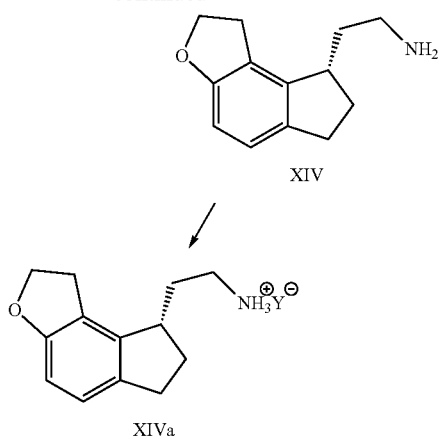

XIV

↓

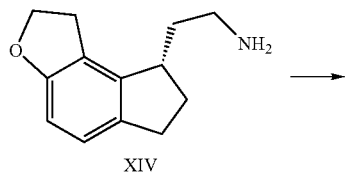

XIVa

In Formula XIV, Y⁻ is an anion, preferably a pharmaceutically acceptable anion, including but not limited to oxalate, sulphate, nitrate, phosphate, perchlorate, borate, halide, acetate, trifluoroacetate, tartrate, maleate, citrate, fumarate, succinate, palmoate, methanesulphonate, benzoate, salicylate, benzenesulfonate, ascorbate, glycerophosphate, and ketoglutarate.

In one embodiment, the present invention encompasses a process for preparing ramelteon, by preparing the compound of Formula XIV as described above, and converting it to ramelteon.

In another embodiment, the present invention encompasses a process for preparing ramelteon of formula I, comprising reacting the compound of formula XIV with propionyl chloride and base to produce ramelteon of Formula I.

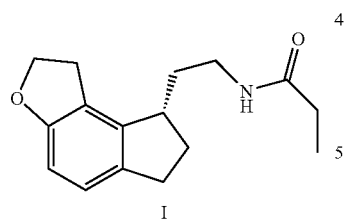

In another embodiment, the present invention encompasses a non-electrostatic crystalline form (herein designated "Form A") of ramelteon, and a process for the preparation of ramelteon Form A which comprises recrystallization of rameleteon from toluene. Preferably, the process comprises dissolving ramelteon in toluene, at a temperature of about 40° C. to about 45° C., followed by concentration of the solution and precipitation of the solute, to obtain the non-electrostatic crystalline form Form A of ramelteon.

In another embodiment, the present invention encompasses a simple and high-yielding process for the preparation of ramelteon, comprising:

(a) Reacting the compound of formula II with malonic acid of formula III to form compound IV;

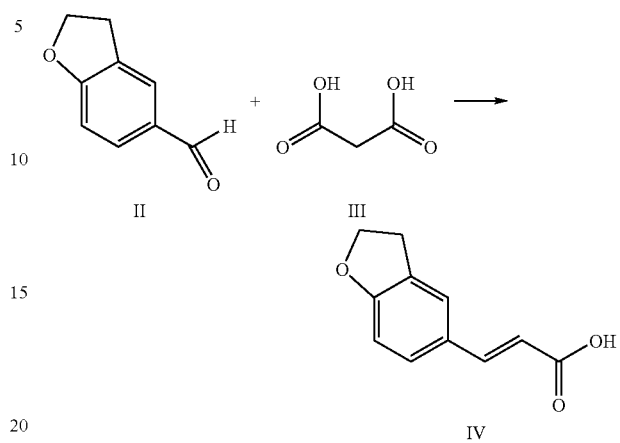

(b) reducing the compound of formula IV to obtain the compound of formula V;

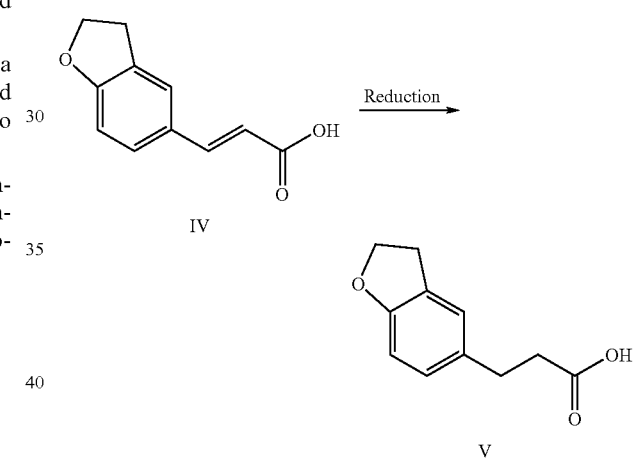

(c) halogenating, preferably brominating, the compound of formula V to form the compound of formula VI;

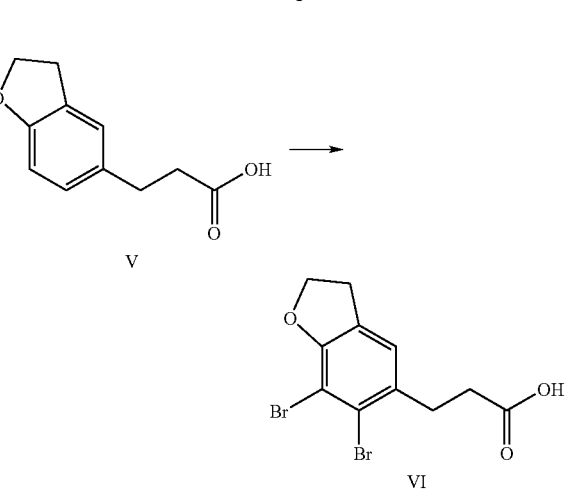

(d) cyclizing the compound of formula VI to produce the compound of formula VII;

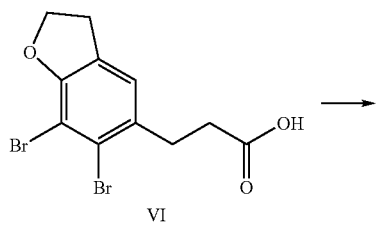

(e) reductively debrominating the compound of formula VII to produce the compound of formula VIII;

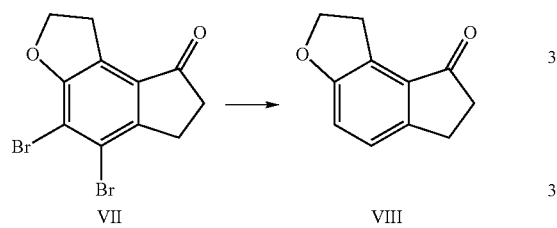

(f) reacting the compound of formula VIII with a compound of formula IX to produce a compound of formula X,

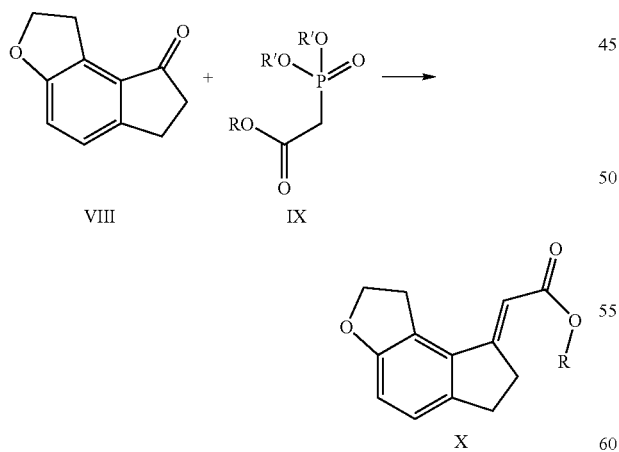

wherein R and R' are independently $C_1$ to $C_6$ straight or branched alkyl, $C_6$ to $C_{10}$ aryl, or $C_7$ to $C_{12}$ arylalkyl. Preferably, R is $C_1$ to $C_4$ straight or branched alkyl, phenyl or benzyl, more preferably methyl or ethyl. R and R' are preferably the same.

(g) hydrolyzing the compound of formula X, followed by reduction of the double bond to obtain the compound of formula XI; or reducing the double bond of the compound of formula X followed by hydrolysis; to produce the compound of formula XI;

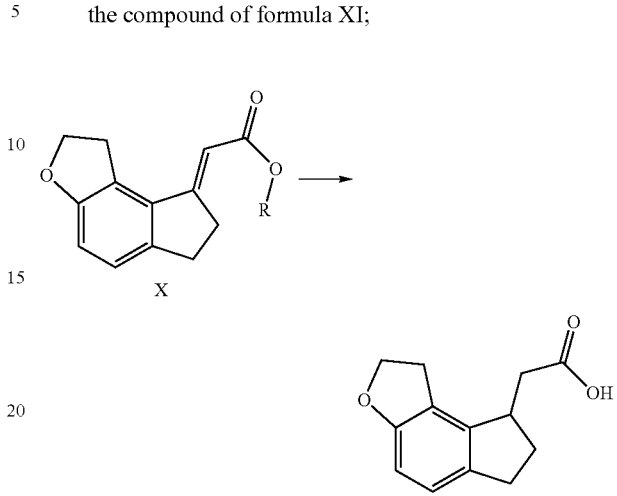

(h) resolving the compound of formula XI by diastereomeric crystallization of a organic chiral amine salt, and acidifying to form the compound of formula (S)-XII.

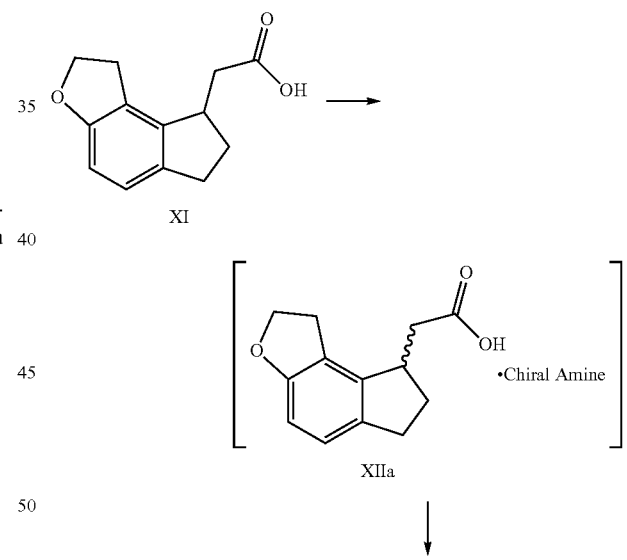

converting the compound of formula (S)-XII to an activated acid derivative, followed by ammoniolysis of the activated acid derivative to produce the compound of formula XIII.

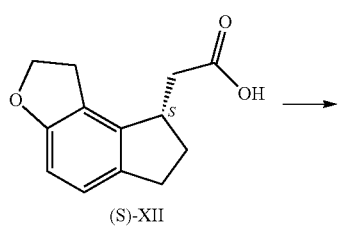

(S)-XII

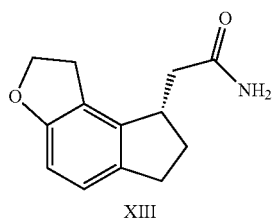

XIII (i) reducing the compound of formula XIII with a reducing agent to form the compound of formula XIV:

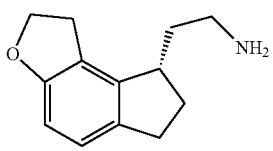
XIV optionally converting the compound of formula XIV to a salt of formula XIVa wherein Y is an anion of an acid

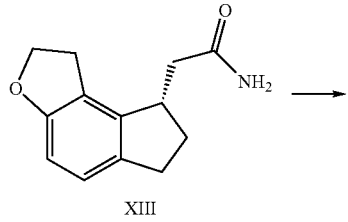
XIII

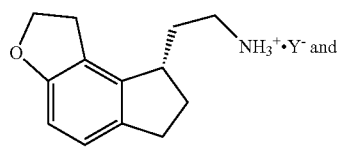

(j) reacting the free base of formula XIV or the salt of XIV with propionyl chloride to form ramelteon of formula I.

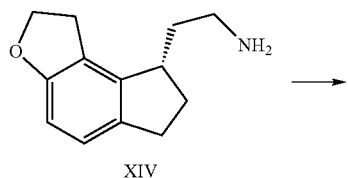
XIV

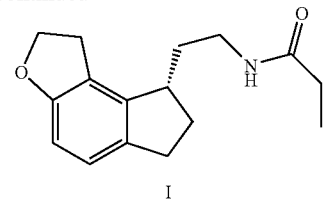
I

DETAILED DESCRIPTION OF THE INVENTION

Figure 1:
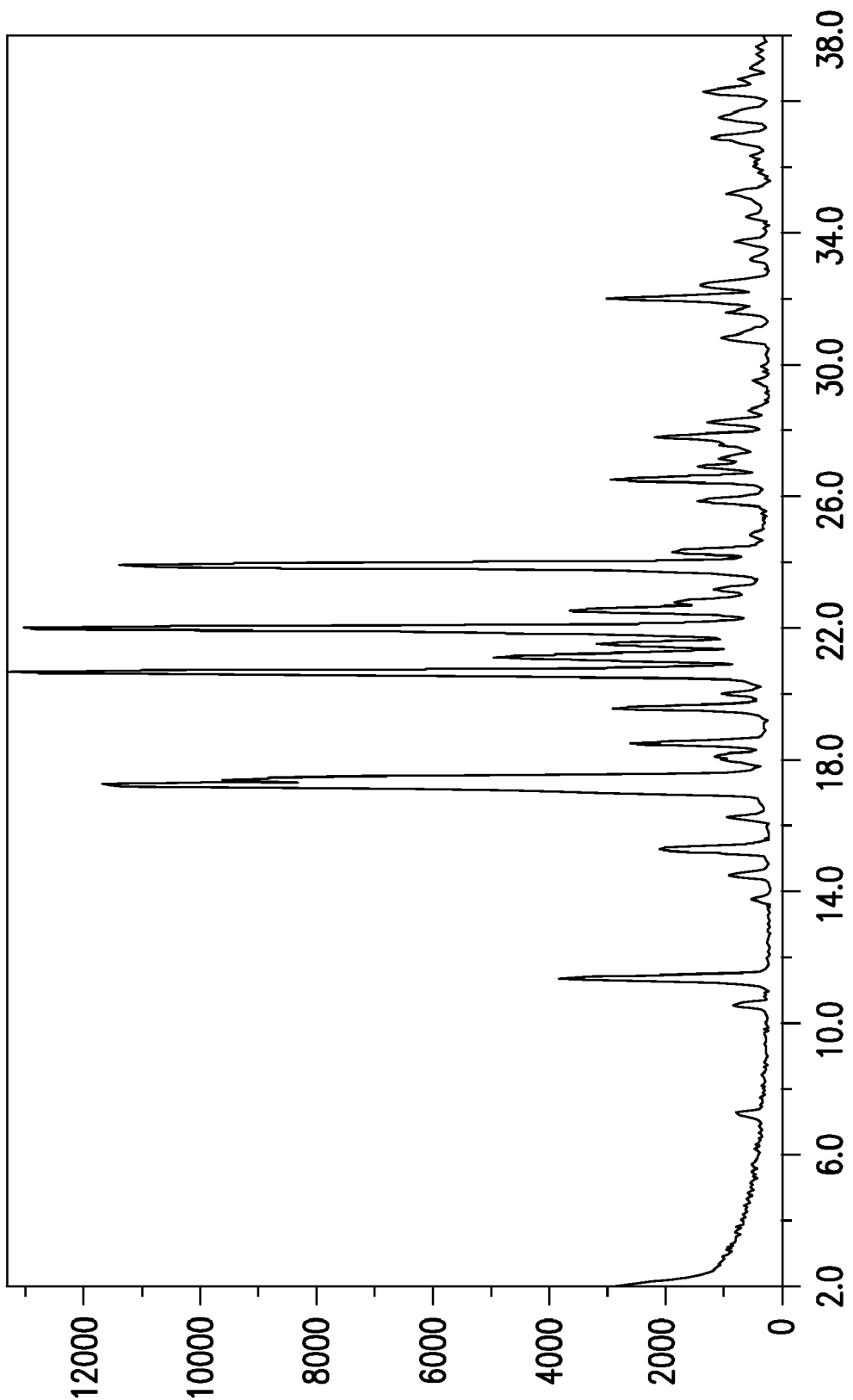
FIG. 1 is the powder X-ray diffractogram of compound (S)-XII, Form I.

As used herein, "non-electrostatic crystalline" refers to the reduced tendency of the crystals to store electrostatic charges. This feature makes the crystals easier and safer to manipulate.

As used herein, "ammonia" includes aqueous ammonia, liquid ammonia and gaseous ammonia. Aqueous ammonia is preferably about 5-35% aqueous ammonia.

As used herein, the term "halogenated hydrocarbon" refers to cyclic or acyclic, saturated or unsaturated aliphatic or aromatic hydrocarbons having at least one halogen substituent. Examples of halogenated hydrocarbons include, but are not limited to, halogenated alkanes such as chloromethane, dichloromethane, carbon tetrachloride, chloroethane, dichlorotrifluoroethane, difluoroethane, hexachloroethane, pentafluoroethane, halogenated alkenes such as such as tetrachloroethene, dichloroethene, trichloroethene, vinyl chloride, chloro-1,3-butadiene, chlorotrifluoroethylene, or halogenated benzenes such as benzotrichloride, benzyl chloride, bromobenzene, chlorobenzene, chlorotoluene, dichlorobenzene, fluorobenzene, or trichlorobenzene. The preferred halogens are chlorine and bromine. The preferred halogenated hydrocarbons are aromatic hydrocarbons or $C_1$-$C_4$ alkanes, and more preferably chlorinated aromatic hydrocarbons or $C_1$-$C_4$ alkanes. The more preferred halogenated hydrocarbons are chlorobenzene, o- or p-dichlorobenzene, dichloromethane, and o-chlorotoluene.

Acids, nitriles and esters are referred to herein by the total number of carbons in the side chains, neglecting the carboxyl carbon. Thus acetic acid is a "$C_1$ acid", propionitrile is a "$C_2$ nitrile", and ethyl acetate is a "$C_3$ ester".

As used herein, the term "organic chiral amine" refers to natural and synthetic chiral amines capable of forming salts with organic carboxylic acids, preferably those known in the art to be useful in the resolution of organic carboxylic acids by the crystallization of diastereomeric salts. A suitable chiral amine is a chiral amine that forms diastereomeric crystalline salts with the enantiomers of compound X which have different solubilities in at least one solvent or solvent mixture. Suitable amines include, but are not limited to, amines of structures 1 and 2 below

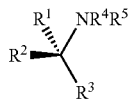

1

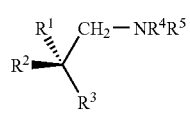

wherein $R^1$ through $R^5$ are independently H, $C_1$-$C_{10}$ alkyl, $C_6$-$C_{10}$ aryl, or $C_5$-$C_9$ heteroaryl, and $R^1$, $R^2$, and $R^3$ are all different from one another. Suitable examples include, but are not limited to, (R)-1-phenylethylamine, (S)-1-phenylethylamine, (R)-1-(4-methylphenyl)ethylamine, (S)-1-(4-methylphenyl)ethylamine, (R)-1-(2-methoxyphenyl)ethylamine, (S)-1-(2-methoxyphenyl)ethylamine, (R)-1-(3-methoxyphenyl)ethylamine, (S)-1-(3-methoxyphenyl)ethylamine, (R)-1-(4-methoxyphenyl)ethylamine, (S)-1-(4-methoxyphenyl)ethylamine, (R)-1-(4-chlorphenyl)ethylamine, (S)-1-(4-chlorphenyl)ethylamine, (R)-1-(3-chlorophenyl)ethylamine, (S)-1-(3-chlorophenyl)ethylamine, (R)-1-(3-bromophenyl)ethylamine, (S)-1-(3-bromophenyl)ethylamine, (R)-1-(4-bromophenyl)ethylamine, (S)-1-(4-bromophenyl)ethylamine, (R)-1-(4-fluorphenyl)ethylamine, (S)-1-(4-fluorphenyl)ethylamine, (R)-1-(3,4-dimethoxyphenyl)ethylamine, (S)-1-(3,4-dimethoxyphenyl)ethylamine, (R)-1-(1-naphthyl)ethylamine, (S)-1-(1-naphthyl)ethylamine, (R)-1-aminotetralin, (S)-1-aminotetralin, (R)-1-aminoindane, (S)-1-aminoindane, (R)-1-(2-naphthyl)ethylamine, (S)-1-(2-naphthyl)ethylamine, (R)-3-methyl-2-butylamine, (S)-3-methyl-2-butylamine, (R)-2-hexylamine, (S)-2-hexylamine, (R)-2-heptylamine, (S)-2-heptylamine, (R)-2-octylamine, (S)-2-octylamine, (R)-2-nonylamine, (S)-2-nonylamine, (R)-3,3-dimethyl-2-aminobutane, (S)-3,3-dimethyl-2-aminobutane, (R)-1-cyclopropylethylamine, (S)-1-cyclopropylethylamine, (R)-1-cyclohexylethylamine, (S)-1-cyclohexylethylamine, (R)-1-phenylpropylamine, (S)-1-phenylpropylamine, (R)-1-phenylbutylamine, (S)-1-phenylbutylamine, (S)-1-methoxy-2-aminopropane, (1R-trans)-2-(phenylmethoxy)cyclopentylamine, (1S-trans)-2-(phenylmethoxy)cyclopentaneamine, (1R-trans)-2-(phenylmethoxy)cyclohexylamine, (1S-trans)-2-(phenylmethoxy)cyclohexylamine, (R)—N-benzyl-1-phenylethylamine, (S)—N-benzyl-1-phenylethylamine, (R,R)-bis-(1-phenylethyl)amine, (S,S)-bis-(1-phenylethyl)amine, (R)-1-phenylethylhydroxylamine, (S)-1-phenylethylhydroxylamine, (1R,2R)-ephedrine, (1S,2S)-ephedrine, (1R,2S)-ephedrine, and (1S,2R)-ephedrine.

Most preferably, the chiral amine is (R)-1-phenylethylamine or (S)-1-phenylethylamine.

In one embodiment, the present invention provides a novel process for producing ramelteon intermediate of formula IV, comprising a Doebner-Knoevenagel condensation between the compound of Formula II and malonic acid (formula III).

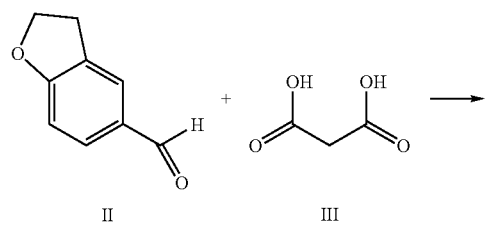

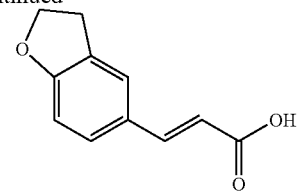

Preferably, the reaction is carried out in the presence of a base, either with a solvent or neat (without a solvent), and optionally in the presence of acetic acid. The reaction is conducted at a temperature of about 0° C. to about 250° C.; preferably about 50-100° C. The reaction time is generally 1 hr to 10 hr; preferably 1 hr to 8 hr, and most preferably 4-5 hr.

Bases useful in the practice of the present invention include, but are not limited to, alkali metal and alkaline earth carbonates, hydroxides and hydrides, for example potassium bicarbonate, sodium bicarbonate, potassium carbonate, sodium carbonate, sodium hydroxide, potassium hydroxide, sodium hydride, potassium hydride, calcium hydroxide, and the like; primary, secondary, and tertiary amines such as piperidine, triethylamine, diisopropylethylamine, N-methylmorpholine and the like; ammonia and ammonium salts; and pyridine, lutidine, and the like. Suitable solvents include, but are not limited to, pyridine, DMF, NMP, DMSO, toluene, and the like. Piperidine and pyridine are preferred bases, and pyridine may serve as both solvent and base.

In another embodiment, the present invention encompasses a process for preparing a ramelteon intermediate of formula V, comprising reduction of compound of formula IV.

The reaction may be carried out by catalytic reduction with hydrogen in presence of a catalyst such as Pd—C or Raney-Ni, or by reduction with a metal such as Zn or Fe in an acidic solvent, such as acetic acid or aqueous HCl.

In catalytic reduction, the hydrogen pressure may be in the range of 0.1 to 100 kg/cm²; preferably 5-10 kg/cm². Alternatively, transfer hydrogenation with Pd—C, using formate as a hydrogen source, for example ammonium formate or sodium formate in an aqueous solvent, may be employed. Alternatively, the reduction of the compound of formula IV may be carried out with Zn/HCl, Fe/HCl, or the like.

The preferred reducing conditions are formate/Pd—C, $H_2$/Raney-Ni, Zn/HCl, and Fe/HCl. Preferably, the reaction is carried out at a temperature between 10° C. and 50° C., more preferably at 25° C. The reaction is conducted in any suitable solvent, which may for example be selected from the group consisting of halogenated hydrocarbons, $C_6$ to $C_{14}$ aromatic hydrocarbons, $C_1$ to $C_5$ alcohols, $C_2$ to $C_7$ esters, $C_4$ to $C_7$ ethers, $C_1$ to $C_5$ carboxylic acids, water, or suitable mixtures of these solvents. Preferred solvents are water, methanol, isopropyl alcohol, dichloromethane, toluene, ethyl acetate, and diethyl ether.

In another embodiment, the present invention encompasses a process for preparing a ramelteon intermediate of formula VI, comprising reacting the compound of formula V with a halogenation, preferably brominating agent.

The solvent may be selected from the group consisting of $C_6$ to $C_{14}$ aromatic hydrocarbons, $C_1$ to $C_5$ aliphatic hydrocarbons, $C_1$ to $C_5$ alcohols, $C_4$ to $C_7$ ethers, $C_1$-$C_7$ acids, halogenated hydrocarbons, or suitable mixtures thereof. Preferable solvents are dichloromethane, ethyl acetate, acetonitrile, methanol and acetic acid. The most preferable solvents are methanol and acetic acid. Halogenation agents include but are not limited to, $Br_2$, $Cl_2$ and $I_2$. Most preferably the halogenation agent is $Br_2$. The brominating agent is used in an amount of 2 to 7 moles per mole of the compound of formula V; preferably about 2 to 5 moles.

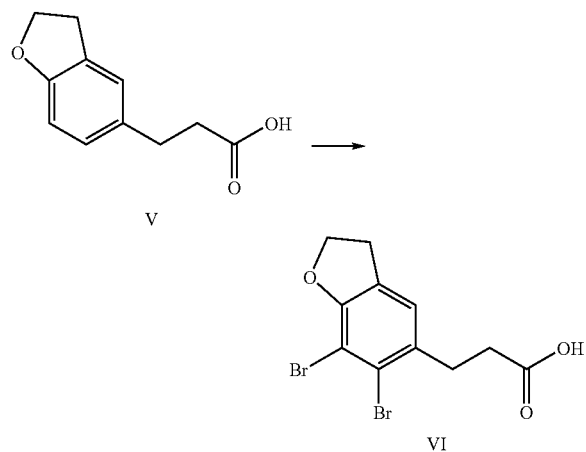

The reaction may be carried out in the presence of a solvent. Preferably, the reaction is conducted in the presence of an acid and/or alkali metal salt of an acid. Suitable acids include organic and inorganic acids, preferably an organic acid selected from the group consisting of acetic acid, formic acid, methanesulfonic acid, and benzoic acid. Suitable inorganic acids include hydrochloric acid, hydrobromic acid, phosphoric acid, and the like. Alkali metal salts of organic acid include, but are not limited to, sodium acetate, potassium acetate, and the like. Alkali metal salts of inorganic acids include, but are not limited to, sodium phosphate, potassium phosphate, and the like.

In another embodiment, the present invention encompasses a process for preparing the ramelteon intermediate of formula VII, comprising cyclizing the compound of formula VI to produce the compound of formula VII.

Though not to be limited to any mechanism, the cyclization is preferably carried out by activating the carboxylic acid group of compound VI, followed by intramolecular acylation of the aryl ring to form compound VII.

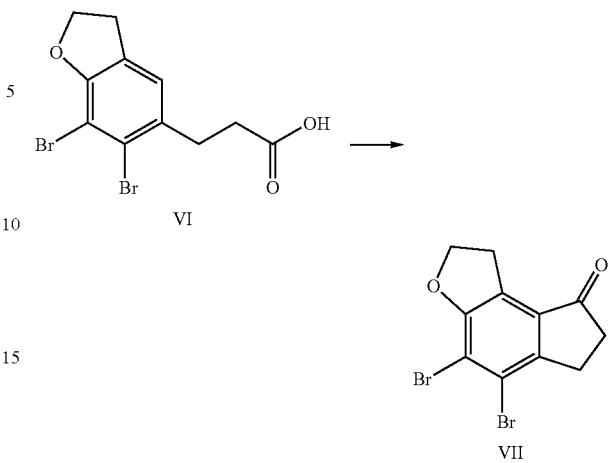

Cyclization may be conducted under Friedel-Crafts conditions known in the art. Suitable catalysts include, but are not limited to, $BF_3$, $AlCl_3$, HF, and the like, preferably $AlCl_3$. The cyclization is conducted in either the absence of a solvent, or the presence of a solvent inert to the reaction. Suitable solvents include, but are not limited to, halogenated hydrocarbons such as o-dichlorobenzene and 1,2-dichloroethane, 1,2,3,4-tetrahydronaphthalene, polar solvents such as NMP and DMF, and mixtures thereof. The reaction is conducted at a temperature of about 0° C. to about 250° C.; preferably about 10-90° C. The reaction time is generally about 1 hr to 10 hr; preferably 1 hr to 8 hr and most preferably about 6-8 hr.

Activation of the carboxylic acid may be carried out with any suitable reagent known for the purpose. Suitable reagents include, but are not limited to, phosphorus oxychloride, phosphorous pentachloride, phosphorus pentoxide, thionyl chloride, phosgene, oxalyl chloride, and the like. Thionyl chloride is preferred. The reaction can be conducted in either the absence of a solvent or in a solvent inert to the reaction. The reaction temperature is generally about 10-150° C.; preferably about 10 to 50° C. Suitable solvents include $C_{6-12}$ aromatic hydrocarbons, $C_{4-7}$ saturated hydrocarbons, ethers such as tetrahydrofuran, dioxane, 1,2-dimethoxyethane, etc.; amides such as N,N-dimethylformamide, N,N-dimethylacetamide, etc. halogenated hydrocarbons such as dichloromethane, dichloroethane, chloroform, carbon tetrachloride, dichlorobenzene etc., anhydrides such as acetic anhydride, etc.; sulfoxides, such as dimethylsulfoxide etc., or mixture thereof. The reaction time is generally about 1 hr to 9 hr, preferably about 1 hr to 4 hr.

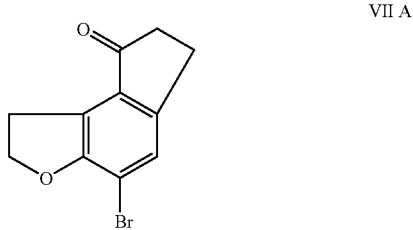

VII A

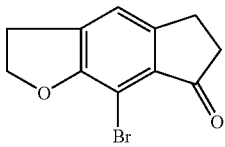

VII B

The impurities VIIA and VIIB are formed during the process of preparation of compound of formula VII from the compound of formula VI. Removal of these impurities from the compound VII results in a good yield of the desired compound. These impurities can also be isolated, such as from compound VII. One embodiment of the present invention provides each of these impurities with a purity of greater than about 50% as measured by HPLC.

The intermediate compound of structure VIII may be prepared by reductive dehalogenation of the compound of formula VII:

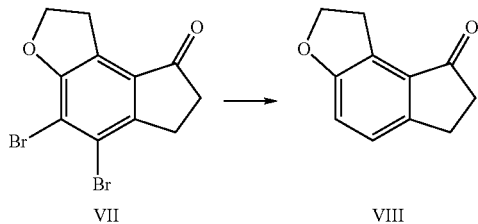

VII     VIII

The reaction can be carried out, for example by reduction with $H_2$/Pd—C, $H_2$/Raney-Ni, Zn/HCl, and Fe/HCl. The preferred method is catalytic reduction with hydrogen, in the presence of a Pd—C catalyst. In catalytic hydrogenations, the hydrogen pressure is about 0.1 kg/cm$^2$ to about 100 kg/cm$^2$; preferably about 5-10 kg/cm$^2$. The reaction is conducted in a solvent selected from the group comprising of $C_6$ to $C_{14}$ aromatic hydrocarbons, $C_1$ to $C_5$ alcohols, $C_2$ to $C_7$ esters, $C_1$ to $C_5$ carboxylic acids, $C_2$ to $C_6$ ethers, water, or suitable mixtures thereof, preferably methanol, isopropyl alcohol, toluene, ethyl acetate, or diethyl ether. The reaction temperature is generally about 15-100° C.; preferably about 20-40° C. The reaction time is generally about 1 hr to about 8 hr; preferably about 2 hr to about 4 hr. Typically, the amount of catalyst used is about 2-30 g per 100 g of the compound of formula VII; preferably about 5-20 g per 100 g of the compound of formula VII.

VIII A

VIII B

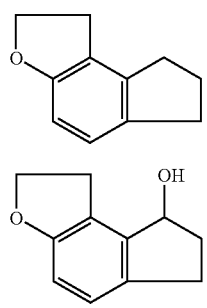

The above two impurities appear during the preparation of compound of the formula VIII from the compound of the formula VII. Removal of such impurities improves the yield of the desired compound. These impurities can also be isolated, such as from compound VIII. One embodiment of the present invention provides each of these impurities with a purity of greater than about 50% as measured by HPLC.

In one embodiment, the present invention provides a compound having the Formula X, its Z isomer of Formula (Z)-X, and mixture thereof,

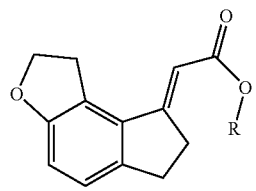

X

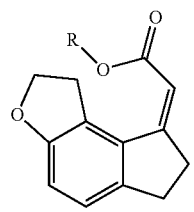

(Z)-X wherein R is $C_1$ to $C_6$ straight or branched alkyl, $C_6$ to $C_{10}$ aryl, and $C_7$ to $C_{12}$ arylalkyl. Preferably, R is $C_1$ to $C_6$ straight or branched alkyl, phenyl or benzyl, more preferably methyl or ethyl.

Preferably, the compound of formula X is isolated, although it need not be separated from the Z isomer (Z)-X. Compound X can be isolated from one or more of compound VIII, compound IX, and the reaction mixture forming compound X. The isolated compound X preferably has a purity of above about 50%, more preferably above about 75%, and most preferably about 90% to about 95% as measured by HPLC.

In one embodiment, the present invention provides a process for producing a ramelteon intermediate of formula X, comprising the step of reacting the compound of Formula VIII with a compound of formula IX in the presence of a base and an organic solvent:

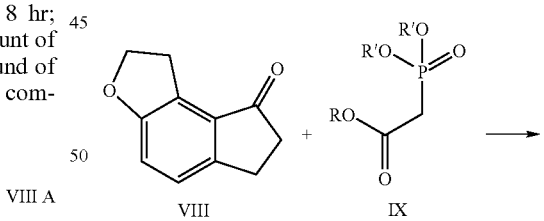

VIII     IX

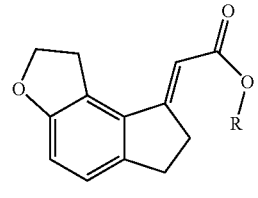

X wherein R and R' are independently $C_1$ to $C_6$ straight or branched alkyl, $C_6$ to $C_{10}$ aryl, or $C_7$ to $C_{12}$ arylalkyl. Preferably, R is $C_1$ to $C_4$ straight or branched alkyl, phenyl or benzyl, more preferably methyl or ethyl. R and R' are preferably the same.

Bases useful in the practice of the present invention include alkali metal hydroxides or hydrides, for example sodium hydroxide, potassium hydroxide, sodium hydride, potassium hydride, and the like; metal amides, for example, sodium amide, lithium diisopropylamide, lithium hexamethyldisilazide, and the like; metal alkoxides, for example, sodium methoxide, sodium ethoxide, potassium t-butoxide, and the like; alkyllithiums such as BuLi; and strong amine bases such as 1,8-diazabicyclo[5.4.0]-undec-7-ene. NaH is a preferred base for use in the practice of the present invention.

The solvent may be selected from the group consisting of $C_{6-10}$ substituted aromatic hydrocarbons, $C_5$ aliphatic hydrocarbons, halogenated hydrocarbons, cyclic ethers, ketones, esters, nitriles, $C_{4-6}$ straight, branched or cyclic hydrocarbons, dioxane, DMF, DMSO, and mixtures thereof. Preferred $C_{6-10}$ substituted aromatic hydrocarbons are toluene and xylene.

Compound X can be isolated from the reaction mixture by adding water to the reaction mixture to obtain two phases, separating the organic layer, and evaporating the organic layer to obtain a residue. Evaporation can be carried out at an elevated temperature of about 50 to about 60° C. and/or a pressure of less than about one atmosphere.

In one embodiment, the present invention encompasses a process for preparing ramelteon, by preparing the compound of Formula X (isolated or not) as described above, and converting it to ramelteon.

In one embodiment, the present invention provides a compound having the Formula Xa in racemic form, as an isolated enantiomer, or a mixture thereof:

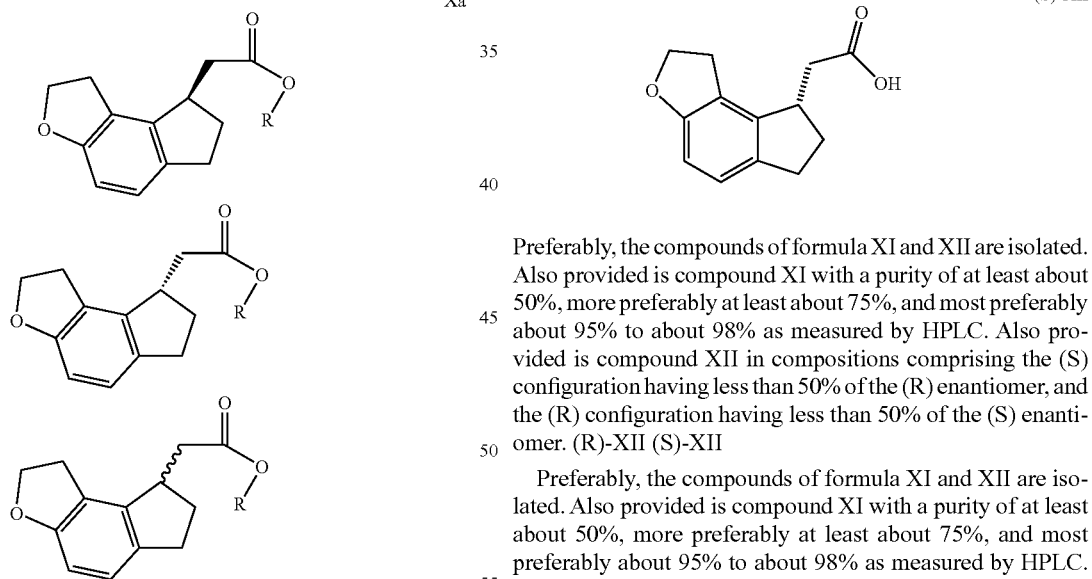

wherein R is $C_1$ to $C_6$ straight or branched alkyl, $C_6$ to $C_{10}$ aryl, and $C_7$ to $C_{12}$ arylalkyl. Preferably, R is methyl, ethyl, phenyl or benzyl.

Compound Xa can be prepared by reduction of compound X. Preferably, the compound of formula Xa, whether in racemic form or enantiomerically enriched form, is isolated. In one embodiment, compound Xa is isolated from compound X and/or the reaction mixture in which it is formed from compound X. In one embodiment, compound XI is isolated from compounds X or Xa. Also provided is compound Xa with a purity of at least about 50% as measured by HPLC. Also provided is compound Xa in a composition comprising the (S) configuration having less than 50% of the (R) enantiomer, or (R) configuration having less than 50% of the (S) enantiomer.

In another embodiment, the present invention provides a racemic compound having the Formula XI:

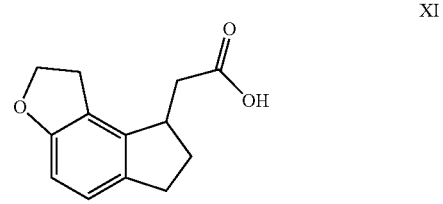

The enantiomers of compound XI, designated XII, have the following structures:

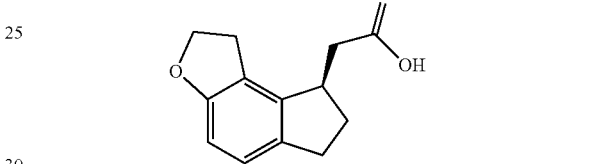

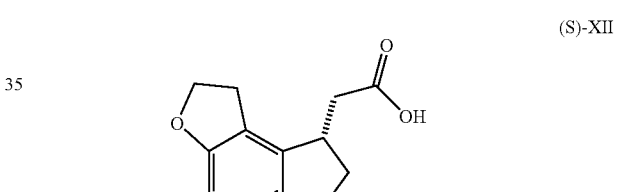

Preferably, the compounds of formula XI and XII are isolated. Also provided is compound XI with a purity of at least about 50%, more preferably at least about 75%, and most preferably about 95% to about 98% as measured by HPLC. Also provided is compound XII in compositions comprising the (S) configuration having less than 50% of the (R) enantiomer, and the (R) configuration having less than 50% of the (S) enantiomer. (R)-XII (S)-XII Preferably, the compounds of formula XI and XII are isolated. Also provided is compound XI with a purity of at least about 50%, more preferably at least about 75%, and most preferably about 95% to about 98% as measured by HPLC. Also provided is compound XII in compositions comprising the (S) configuration having less than 50% of the (R) enantiomer, and the (R) configuration having less than 50% of the (S) enantiomer.

In another embodiment, the present invention encompasses a process for preparing the ramelteon intermediate of formula XI, comprising hydrolysis of compound of formula X, followed by reduction of the double bond In another alternative embodiment, the present invention encompasses another process for preparing compound of formula XI comprising reducing the double bond in the compound of formula X, followed by hydrolysis.

Reduction of the double bond may be carried out by catalytic reduction with hydrogen in the presence of Pd—C or Raney-Ni, or reduction with Zn/HCl or Fe/HCl. The hydrogen used in the catalytic reduction is in the range of about 0.1 kg/cm$^2$ to 100 kg/cm$^2$; preferably 5-10 kg/cm$^2$. The reaction is conducted in a solvent selected from the group comprising of halogenated hydrocarbons, $C_6$ to $C_{14}$ aromatic hydrocarbons, $C_1$ to $C_5$ alcohols, $C_2$ to $C_7$ esters, $C_4$ to $C_7$ ethers, $C_1$ to $C_5$ carboxylic acids, cyclic ethers, water, and suitable mixtures thereof. Preferred solvents are methanol, isopropyl alcohol, dichloromethane, toluene, ethyl acetate, and diethyl ether. The reaction temperature is generally about 15-100° C.; preferably about 20-40° C. The reaction time is generally about 1 hr to 5 hr; preferably about 1 hr to 3 hr. Typically, the amount of catalyst used is about 2-30 g per 100 g of compound X; preferably about 5-20 g per 100 g of compound X. Preferably, the base for hydrolysis is selected from alkali metal carbonates or hydroxides, for example potassium carbonate, sodium carbonate, sodium hydroxide, and potassium hydroxide, preferably sodium hydroxide. Preferably, the acid is sulfuric acid or hydrochloric acid.

Compound XI can be isolated as a solid, by recovering the precipitate formed, such as by filtration. The isolated compound XI can be dried at elevated temperature of about 50 to about 70° C. and/or a pressure of less than about one atmosphere.

In one embodiment, the present invention encompasses a novel process for preparing ramelteon, by preparing the compound of Formula XI (isolated or not) as described above, and converting it to ramelteon.

In one embodiment, the present invention provides a compound having the Formula XII, which encompasses the individual isomers and non-racemic mixtures thereof:

and further provides chiral amine salts thereof, represented by formula XIIa:

Preferably, the compound of Formula XII including the individual isomers and the racemic mixture is isolated.

Compound XII is preferably isolated from compound XIIa and/or the reaction mixture in which compound XIIa is formed. Compound XII preferably has a chiral purity of more than about 75%, more preferably more than about 75%, and most preferably about 90% to about 100%, as measured by HPLC. Compound XII preferably has a chemical purity of more than about 75%, more preferably more than about 75%, and most preferably about 90% to about 100%, as measured by HPLC.

The salt XIIa is preferably isolated from compound XI and unreacted base used. The filtered product can be dried at a temperature of about 40° C. to about 70° C. and/or a pressure of less than one atmosphere. Compound XIIa, either in (S) or (R) form preferably has a chiral purity of above about 50%, more preferably above about 75% and most preferably about 85% to about 95%. Also provided are compound XII in a composition comprising the (S) configuration having less than 50% of the (R) enantiomer, and compound XII in a composition comprising the (R) configuration having less than 50% of the (S) enantiomer.

In another embodiment, the present invention encompasses a process for preparing the ramelteon intermediate enantiomer of formula (S)-XII, comprising resolution of the racemic form of formula XI by diastereomeric crystallization of an organic chiral amine salt, and acidifying. Typically, (R)-phenylethyl amine is used in order to obtain (S)-XII, and (S)-phenylethyl amine is used in order to obtain (R)-XII.

Salt formation is carried out in the presence of a suitable organic chiral amine in an organic solvent or aqueous organic solvent, to obtain the diastereomeric amine salts of compound of formula XIIa, followed by isolation of a single diastereomer by crystallization and subsequent treatment with acid to form the compound of formula (S)-XII. The diastereomeric amine salt of compound of formula XIIa may be subjected to repeated recrystallizations in order to raise the optical purity of the (S)-XII component.

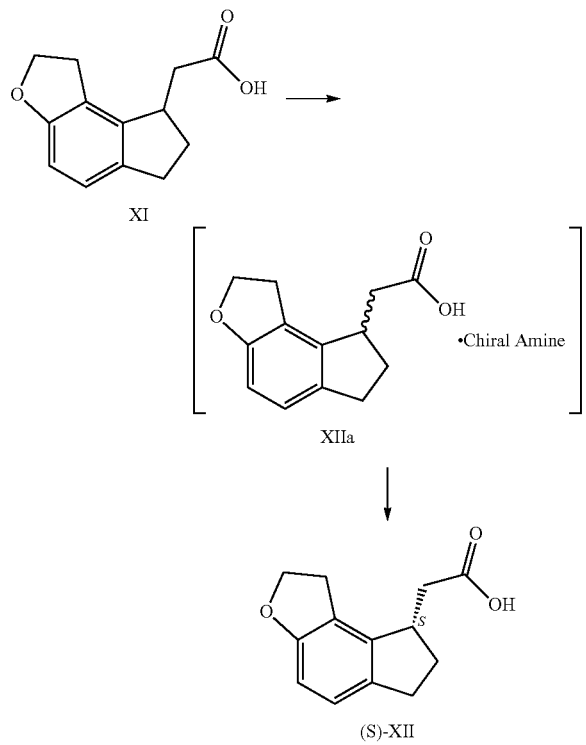

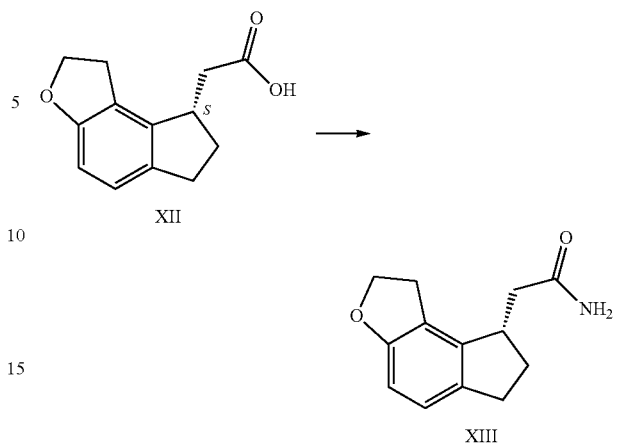

Suitable solvents include, but are not limited to, halogenated hydrocarbons, $C_6$ to $C_{14}$ aromatic hydrocarbons, $C_1$ to $C_5$ alcohols, $C_2$ to $C_7$ esters, $C_4$ to $C_7$ ethers, $C_1$ to $C_5$ carboxylic acids, nitriles, ketones, water, and suitable mixtures thereof. The compound of formula (S)-XII so obtained is preferably in a crystalline form. It is desirable to obtain ramelteon of high enantiomeric purity, therefore the crystalline (S)-XII is preferably exhibits an enantiomeric excess over the racemate of at least 90%, more preferably 98%, and most preferably at least a 99% enantiomeric excess.

In one embodiment, the present invention provides a compound of formula (S)-XII.

In one embodiment, the present invention provides solid compound of formula (S)-XII.

In one embodiment, the present invention provides crystalline compound (S)-XII.

Crystalline compound (S)-XII is characterized by a powder X-ray diffraction pattern with peaks at about 11.3, 15.3, 18.5, 22.0 and 24.3±0.2 degrees 2 theta. Compound (S)-XII crystalline Form I may be further characterized by a PXRD pattern substantially as depicted in FIG. 1.

In one embodiment, the present invention encompasses a process for preparing ramelteon, by preparing the compound of Formula (S)-XII as described above, and converting it to ramelteon.

In another embodiment, the present invention encompasses a process for preparing a ramelteon intermediate of formula XIII, comprising converting the —COOH group to form an activated acid derivative, followed by ammonolysis of the activated acid derivative.

In certain preferred embodiments the activated acid derivative is an acid chloride. Acid chloride formation can be achieved by using thionyl chloride, $POCl_3$, $PCl_3$, $PCl_5$, $SO_2Cl_2$, oxalyl chloride, phosgene, and the like, preferably thionyl chloride. The acid chloride or active ester is treated with ammonia or an ammonia-generating reagent to produce the compound of formula XIII. Suitable organic solvents include, but are not limited to, halogenated hydrocarbons, $C_6$ to $C_{14}$ aromatic hydrocarbons, $C_2$ to $C_7$ esters, $C_4$ to $C_7$ ethers, C1 to C5 nitriles, C3 to C8 ketones, and mixtures thereof; preferably dichloromethane, toluene, ethyl acetate, or diethyl ether.

In other embodiments, the present invention encompasses an alternate process for preparing a ramelteon intermediate of formula XIII, comprising converting the —COOH group to compound of formula XIIb, followed by the ammonolysis of the activated acid derivative.

An active ester or mixed anhydride of compound (S)-XII may be prepared by any of the methods known in the art, for example by treatment with ethyl or methyl chloroformate, pivaloyl chloride, or a carbodiimide. One such embodiment comprises introducing a solution of an activated carbonate such as ethyl chloroformate into a solution of compound (S)-XII in an organic solvent in the presence of a base, so as to obtain a mixed anhydride such as XIIb; followed by contacting the mixed anhydride with ammonia generating reagent.

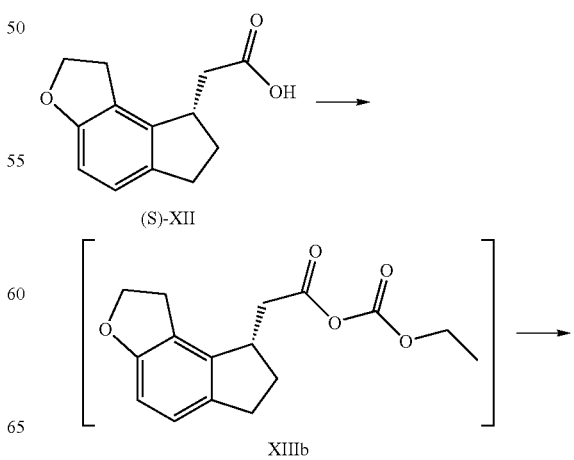

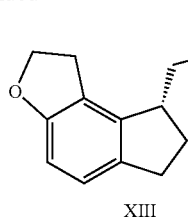

XIII

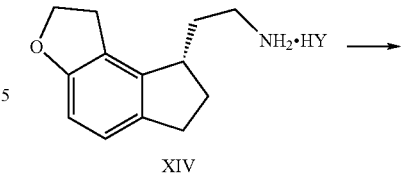

XIV

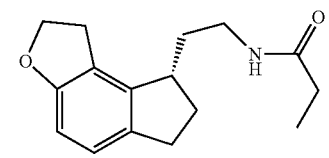

I

Suitable organic solvents include, but are not limited to, halogenated hydrocarbons, $C_6$ to $C_{14}$ aromatic hydrocarbons, $C_2$ to $C_7$ esters, $C_4$ to $C_7$ ethers, cyclic ethers, and mixture thereof; preferably dichloromethane, dichloroethane, toluene, ethyl acetate, or diethyl ether; most preferably dichloromethane. The organic base may be selected from the group consisting of triethylamine, diisopropylethylamine, N-methylmorpholine, pyridine, lutidine, and picoline, most preferably triethylamine.

The active ester or mixed anhydride is preferably formed at a temperature of about −20° C. to about 25° C. Most preferably, the temperature is about −10° C. to about 5° C. The obtained reaction mixture is treated with ammonia or an ammonia-generating reagent to produce compound of formula XIII.

In another embodiment, the present invention encompasses an improved process for preparing the ramelteon intermediate of formula XIV, comprising reduction of compound of formula XIII with an amide reducing agent, followed by formation of a salt of formula XIV.

Preferably, the amide reducing agent can be, for example borane, sodium borohydride in presence of boron-trifluoride diethyl ether complex in tetrahydrofuran, or an aluminum hydride such as LiAlH$_4$, sodium bis(2-methoxyethoxy)aluminium hydride (Red-Al™) or diisobutylaluminum hydride. The reaction is carried out at about −20° C. to 50° C. The obtained compound is contacted with suitable acid HY in an organic solvent to produce a salt of formula XIV:

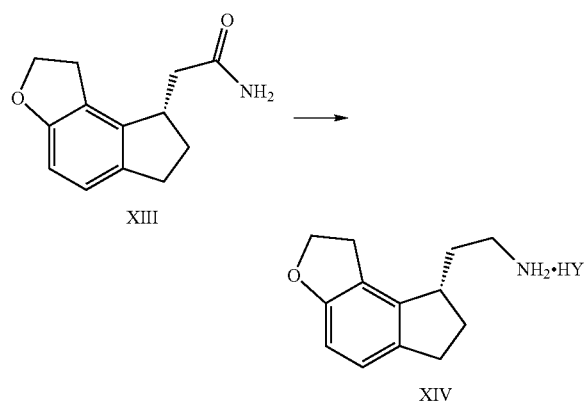

The acid HY preferably forms a pharmaceutically acceptable salt, including but not limited to sulphate, nitrate, phosphate, perchlorate, borate, hydrohalide, acetate, trifluoroacetate, tartrate, maleate, citrate, fumarate, succinate, palmoate, methanesulphonate, benzoate, salicylate, benzenesulfonate, ascorbate, glycerophosphate, and ketoglutarate.

In one embodiment, the present invention encompasses a process for preparing ramelteon, by preparing the compound of Formula XIV as described above, and converting it to ramelteon.

The reaction is carried out in presence of a base and a suitable organic solvent. Suitable organic solvents include, but are not limited to, halogenated hydrocarbons, $C_6$ to $C_{14}$ aromatic hydrocarbons, $C_2$ to $C_7$ esters, $C_4$ to $C_7$ ethers, cyclic ethers, and mixture thereof, preferably dichloromethane, dichloroethane, toluene, ethyl acetate, or diethyl ether; most preferably dichloromethane. The base may be selected from the group consisting of inorganic bases such as sodium carbonate, sodium bicarbonate, potassium carbonate, potassium bicarbonate, and sodium hydroxide, or organic bases such as triethylamine, diisopropylethylamine, N-methylmorpholine, pyridine, lutidine, and picoline, most preferably triethylamine.

In another embodiment, the present invention encompasses a process for preparing non-electrostatic crystalline Form A of ramelteon of formula I, comprising reacting compound of formula XIV with propionyl chloride and crysallization from toluene.

In another embodiment, the present invention encompasses a process for crystallizing ramelteon of formula I, comprising combining ramelteon with a hydrocarbon, preferably a $C_5$-$C_{12}$ aromatic hydrocarbon, most preferably toluene, preferably at a temperature of preferably about 40° C. to about 60° C., more preferably about 40° C. to about 45° C., followed by precipitation of the compound to obtain non-electrostatic crystalline Form A of ramelteon.

The present invention encompasses non-electrostatic crystalline Form A of ramelteon having purity of greater than about 90%, such as about 99.53 to about 99.79% as measured by HPLC.

The material obtained from this process (using toluene) is much more preferable during handling and processing compared to material obtained from ethyl acetate. We have found that material obtained from toluene is much more flowable and much less chargeable than material obtained from ethyl acetate.

The crystalline form preferably has a calculated charge density of less than about 7 nC/gr, more preferably charge density of less than about 5 nC/gr or less than about 3 nC/gr or less than about 1 nC/gr, and most preferably about −3 to about 0 nC/gr.

The crystalline form preferably has an average charge density of less than about 7 nC/gr, more preferably less than about 5 nC/gr or less than about 3 nC/gr and most preferably about 0 to about 2 nC/gr.

The crystalline form preferably has a Basic Flow Energy of less than about 150, more preferably less than about 120, and most preferably about 80 to about 120, mJ.

The crystalline form preferably has a solubility index of above about 0.8, more preferably of about 0.8 to about 1.2.

In another embodiment, the present invention encompasses a novel, simple and high-yielding process for preparing ramelteon, having the Formula I

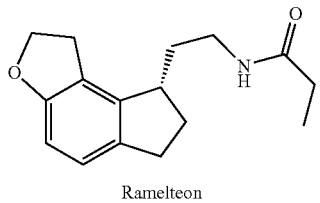

Ramelteon which comprises the steps of:

(a) Reacting the compound of formula I with malonic acid of formula III, to form the compound of formula IV.

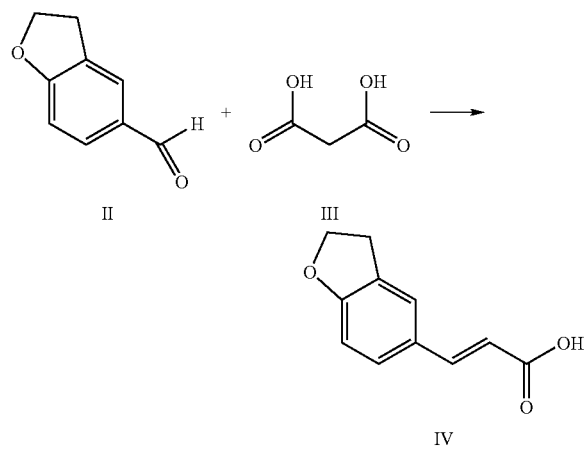

Preferably, the reaction is carried out in the presence of a base, and a solvent, or neat (without a solvent), and optionally in the presence of acetic acid. The reaction is conducted at a temperature of about 0° C. to about 250° C.; preferably about 50-100° C. The reaction time is generally 1 hr to 10 hr; preferably 1 hr to 8 hr, and most preferably 4-5 hr. Suitable bases include, but are not limited to, alkali metal and alkaline earth carbonates, hydroxides or hydrides, for example potassium bicarbonate, sodium bicarbonate, potassium carbonate, sodium carbonate, sodium hydroxide, potassium hydroxide, sodium hydride, potassium hydride, calcium hydroxide, and the like; primary, secondary, and tertiary amines such as piperidine, triethylamine, diisopropylethylamine, N-methylmorpholine and the like; ammonia and ammonium salts; and pyridine, lutidine, and the like. Suitable solvents include, but are not limited to, DMF, NMP, DMSO, toluene, and the like. Piperidine is a preferred base, and pyridine is a preferred solvent, in the practice of the present invention.

(b) Reduction of compound of formula IV to obtain the compound of formula V;

Preferably, the reduction can be carried out using a metal, typically, in the presence of a suitable solvent, for example, by using metal hydrides such as $NaBH_4$ or $LiAlH_4$, catalytic reduction with hydrogen in presence of a catalyst such as Pd—C or Raney-Ni, reduction with a metal such as Zn or Fe in an acidic solvent, such as acetic acid or aqueous HCl, or reduction with a metal hydride such as $NaHB_4$ or $LiAlH_4$.

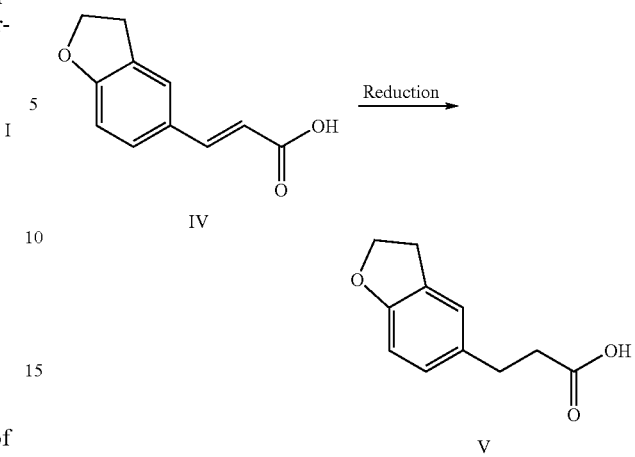

In catalytic reduction, the hydrogen pressure may be in the range of 0.1 to 100 $kg/cm^2$; preferably 5-10 $kg/cm^2$. Alternatively, transfer hydrogenation with Pd—C, using formate as a hydrogen source, for example ammonium formate or sodium formate in an aqueous solvent, may be employed. Alternatively, the reduction of the compound of formula IV may be carried out with Zn/HCl, Fe/HCl, or the like.

The preferred reducing conditions are formate/Pd—C, $H_2$/Raney-Ni, Zn/HCl, and Fe/HCl. The reaction is conducted in any suitable solvent, which may for example be selected from the group consisting of halogenated hydrocarbons, $C_6$ to $C_{14}$ aromatic hydrocarbons, $C_1$ to $C_5$ alcohols, $C_2$ to $C_7$ esters, $C_4$ to $C_7$ ethers, $C_1$ to $C_5$ carboxylic acids, water, or suitable mixtures of these solvents. Preferred solvents are water, methanol, isopropyl alcohol, dichloromethane, toluene, ethyl acetate, and diethyl ether.

(c) Reacting the compound of formula V with an halogenation agent.

Preferably, the reaction is carried out in presence of an acid, and optionally an alkali metal salt of the acid, in a suitable solvent.

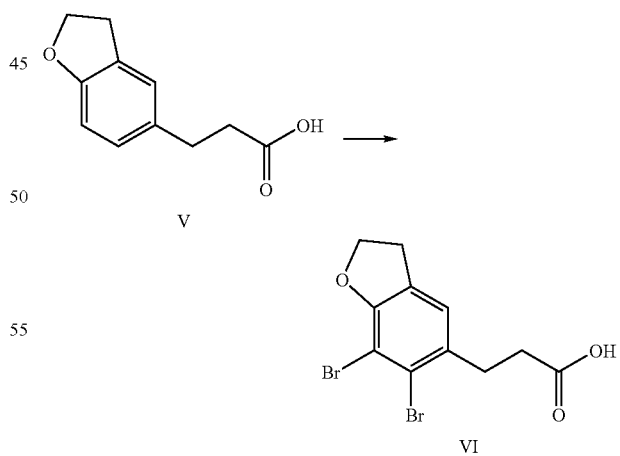

The solvent may be selected from the group consisting of $C_6$ to $C_{14}$ aromatic hydrocarbon, $C_1$ to $C_5$ aliphatic hydrocarbons, $C_1$ to $C_5$ alcohols, $C_4$ to $C_7$ ethers, $C_1$-$C_7$ acids, halogenated hydrocarbons, or suitable mixtures thereof. Preferable solvents are dichloromethane, ethyl acetate, acetonitrile, methanol and acetic acid. The most preferable solvents are methanol and acetic acid. The halogenation agent including but not limited to, $Br_2$, $Cl_2$ and $I_2$. Most preferably the halogenation agent is $Br_2$. The brominating agent is used in an amount of 1 to 7 moles per mole of the compound of formula V; preferably about 2 to 5 moles.

Suitable acids include organic and inorganic acids, preferably an organic acid selected from the group consisting of acetic acid, formic acid, methanesulfonic acid, and benzoic acid. Suitable inorganic acids include hydrochloric acid, hydrobromic acid, phosphoric acid, and the like. Alkali metal salts of organic acid include, but are not limited to, sodium acetate, potassium acetate, and the like. Alkali metal salts of inorganic acids include, but are not limited to, sodium phosphate, potassium phosphate, and the like.

(d) Cyclizing the compound of formula VI to produce compound of formula VII.

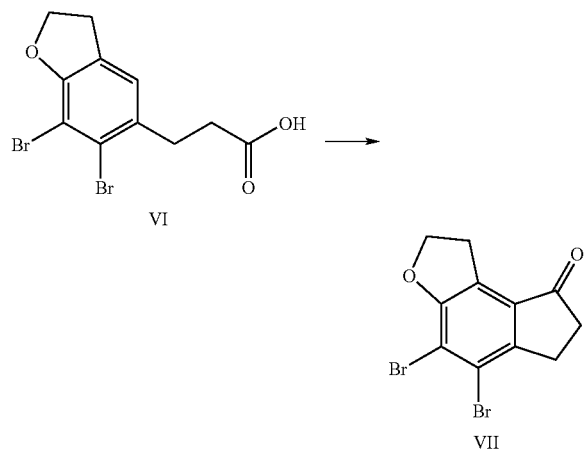

The cyclization is preferably carried out by activating the carboxylic acid group of compound VI, followed by intramolecular acylation of the aryl ring to form compound VII.

The cyclization is conducted in either the absence of a solvent, or the presence of a solvent inert to the reaction. Suitable solvents include, but are not limited to, aromatics solvents such as 1,2,3,4-tetrahydronaphthalene and o-dichlorobenzene, ethers such as diphenyl ether, dimethyleneglycol dimethyl ether, and the like, N,N-dimethylaniline, N,N-diethylaniline, and suitable mixtures of these solvents. The reaction is conducted at a temperature of about 0° C. to about 250° C.; preferably about 10-90° C. The reaction time is generally about 1 hr to 10 hr; preferably 1 hr to 8 hr and most preferably about 6-8 hr.

Activation of the carboxylic acid may be carried out with any suitable reagent known for the purpose. Suitable reagents include, but are not limited to, phosphorus oxychloride, phosphorous pentachloride, phosphorus pentoxide, thionyl chloride, phosgene, oxalyl chloride, and the like. Thionyl chloride is preferred. The reaction can be conducted in either the absence of a solvent or in a solvent inert to the reaction. The reaction temperature is generally about 10-150° C.; preferably about 10 to 50° C. Suitable solvents include $C_{6-12}$ aromatic hydrocarbons, $C_{4-7}$ saturated hydrocarbons, ethers such as tetrahydrofuran, dioxane, 1,2-dimethoxyethane, etc.; amides such as N,N-dimethylformamide, N,N-dimethylacetamide, etc. halogenated hydrocarbons such as dichloromethane, dichloroethane, chloroform, carbon tetrachloride, dichlorobenzene etc., anhydrides such as acetic anhydride, etc.; sulfoxides, such as dimethylsulfoxide etc., or mixture thereof. The reaction time is generally about 1 hr to 9 hr, preferably about 1 hr to 4 hr.

(e) Reductive dehalogenation of the compound of formula VII. The reaction can be carried out for example by reduction with $H_2$/Pd—C, $H_2$/Raney-Ni, Zn/HCl, and Fe/HCl.

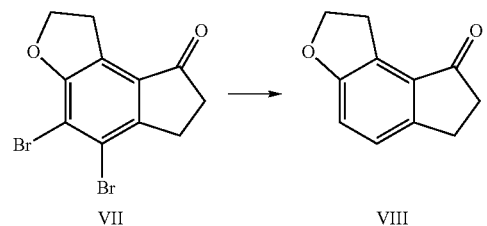

The preferred method is catalytic reduction with hydrogen, in the presence of a Pd—C catalyst. In catalytic hydrogenations, the hydrogen pressure is about 0.1 kg/cm² to about 100 kg/cm²; preferably about 5-10 kg/cm². The reaction is conducted in a solvent selected from the group comprising of $C_6$ to $C_{14}$ aromatic hydrocarbons, $C_1$ to $C_5$ alcohols, $C_2$ to $C_7$ esters, $C_1$ to $C_5$ carboxylic acids, $C_2$ to $C_6$ ethers, water, or suitable mixtures thereof, preferably methanol, isopropyl alcohol, toluene, ethyl acetate, or diethyl ether. The reaction temperature is generally about 15-100° C.; preferably about 20-40° C. The reaction time is generally about 1 hr to about 8 hr; preferably about 2 hr to about 4 hr. Typically, the amount of catalyst used is about 2-30 g per 100 g of the compound of formula VII; preferably about 5-20 g per 100 g of the compound of formula VII.

(f) Condensing the compound of Formula VIII with compound of formula IX in the presence of a base in a suitable organic solvent

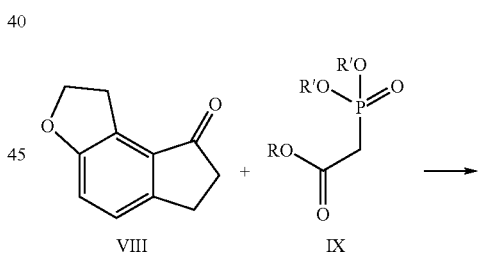

wherein R and R' are independently $C_1$ to $C_6$ straight or branched alkyl, $C_6$ to $C_{10}$ aryl, and $C_7$ to $C_{12}$ arylalkyl. Preferably, R is $C_1$ to $C_6$ straight or branched alkyl, phenyl or benzyl, more preferably methyl or ethyl, and preferably R and R' are the same.

Suitable bases include alkali metal hydroxides or hydrides, for example sodium hydroxide, potassium hydroxide, sodium hydride, potassium hydride, and the like; metal amides, for example, sodium amide, lithium diisopropylamide, lithium hexamethyldisilazide, and the like; metal alkoxides, for example, sodium methoxide, sodium ethoxide, potassium t-butoxide, and the like; alkyllithiums such as BuLi; and strong amine bases such as 1,8-diazabicyclo[5.4.0]undec-7-ene. NaH is the preferred base. The solvent may be selected from the group consisting of $C_{6-10}$ substituted aromatic hydrocarbons, $C_{1-5}$ aliphatic hydrocarbons, halogenated hydrocarbons, cyclic ethers, ketones, esters, nitriles, $C_{4-6}$ straight, branched or cyclic hydrocarbons, dioxane, DMF, DMSO, and mixtures thereof. Preferred $C_{6-10}$ substituted aromatic hydrocarbons are toluene and xylene.

(g) The steps, in either order, of hydrolysis of compound of formula X, and reduction of double bond.

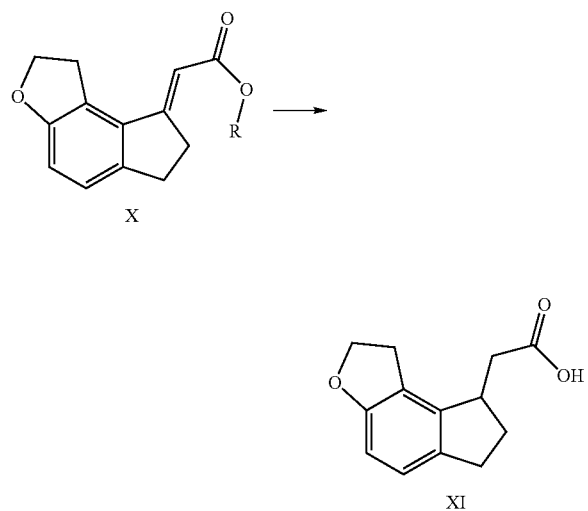

Reduction of the double bond is carried out by catalytic reduction with hydrogen in the presence of Pd—C or Raney-Ni, or reduction with Zn/HCl or Fe/HCl. The hydrogen used in the catalytic reduction is in the range of about 0.1 kg/cm² to 100 kg/cm²; preferably 5-10 kg/cm². The reaction is conducted in a solvent selected from the group comprising of halogenated hydrocarbons, $C_6$ to $C_{14}$ aromatic hydrocarbons, $C_1$ to $C_5$ alcohols, $C_2$ to $C_7$ esters, $C_4$ to $C_7$ ethers, $C_1$ to $C_5$ carboxylic acids, cyclic ethers, water, and suitable mixtures thereof. Preferred solvents are methanol, isopropyl alcohol, dichloromethane, toluene, ethyl acetate, and diethyl ether. The reaction temperature is generally about 15-100° C.; preferably about 20-40° C. The reaction time is generally about 1 hr to 5 hr; preferably about 1 hr to 3 hr. Typically, the amount of catalyst used is about 2-30 g per 100 g of compound X; preferably about 5-20 g per 100 g of compound X. Preferably, the base for hydrolysis is selected from alkali metal carbonates or hydroxides, for example potassium carbonate, sodium carbonate, sodium hydroxide, and potassium hydroxide, preferably sodium hydroxide. Preferably, the acid is sulfuric acid or hydrochloric acid.

(h) resolving the compound of formula XI by diastereomeric crystallization of an organic chiral amine salt, and acidifying to form the compound of formula (S)-XII.

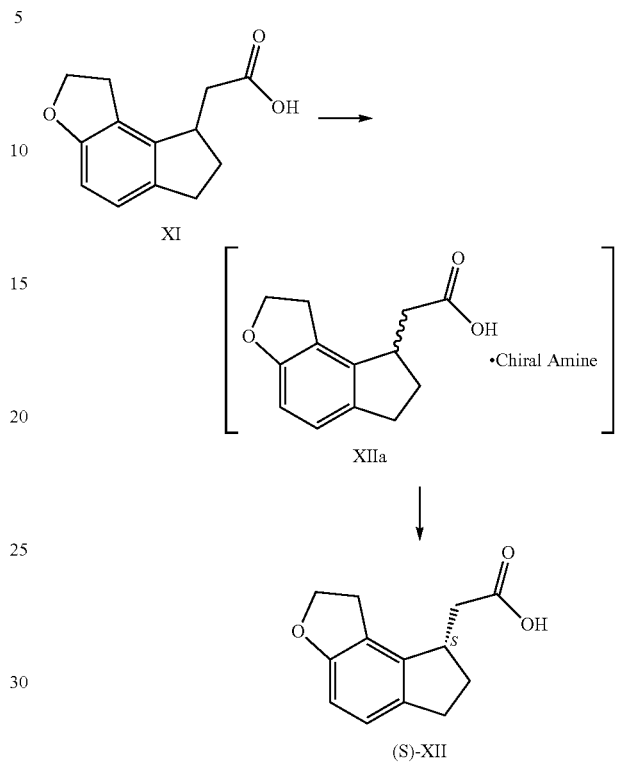

The reaction is carried out in the presence of a suitable solvents include, but are not limited to, halogenated hydrocarbons, $C_6$ to $C_{14}$ aromatic hydrocarbons, $C_1$ to $C_5$ alcohols, $C_2$ to $C_7$ esters, $C_4$ to $C_7$ ethers, $C_1$ to $C_5$ carboxylic acids, nitriles, ketones, water, and suitable mixtures thereof. The compound of formula (S)-XII so obtained is preferably in a crystalline form, and is characterized by a powder X-ray diffraction pattern with peaks at about 11.3, 15.3, 18.5, 22.0 and 24.3±0.2 degrees 2 theta, or by a PXRD pattern substantially as depicted in FIG. 1.

(i) Formation of an active ester, mixed anhydride, or acid chloride of compound (S)-XII, followed by reaction with ammonia or an ammonia-generating reagent such as urea.

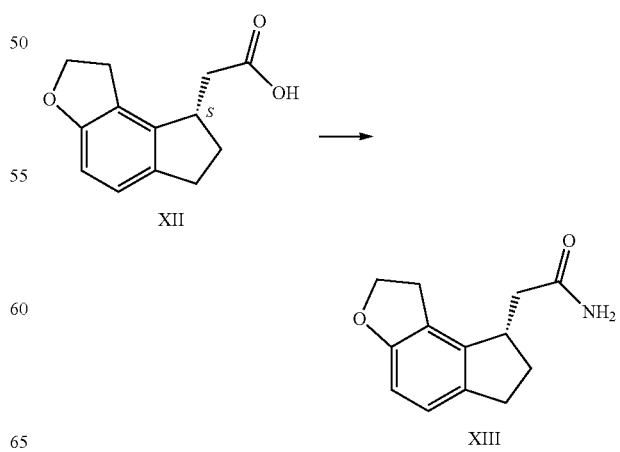

Acid chloride formation is preferred, and can be achieved by using thionyl chloride, POCl$_3$, PCl$_3$, PCl$_5$, SO$_2$Cl$_2$, oxalyl chloride, phosgene, and the like, preferably thionyl chloride. The acid chloride or active ester is treated with ammonia or an ammonia-generating reagent to produce the compound of formula XIII. Suitable organic solvents include, but are not limited to, halogenated hydrocarbons, C$_6$ to C$_{14}$ aromatic hydrocarbons, C$_2$ to C$_7$ esters, C$_4$ to C$_7$ ethers, nitriles, ketones, and mixtures thereof; preferably dichloromethane, toluene, ethyl acetate, or diethyl ether.

An active ester or mixed anhydride of compound (S)-XII is prepared by any of the methods known in the art, for example by treatment with ethyl or methyl chloroformate, pivaloyl chloride, or a carbodiimide. One such embodiment comprises introducing a solution of an activated carbonate such as ethyl chloroformate into a solution of compound (S)-XII in an organic solvent in the presence of a base, so as to obtain a mixed anhydride such as XIIb; followed by contacting the mixed anhydride with ammonia.

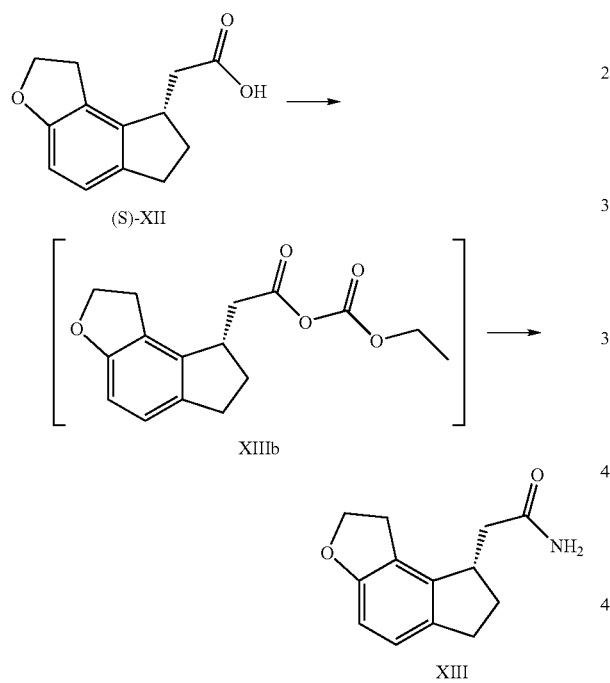

Suitable organic solvents include, but are not limited to, halogenated hydrocarbons, C$_6$ to C$_{14}$ aromatic hydrocarbons, C$_2$ to C$_7$ esters, C$_4$ to C$_7$ ethers, cyclic ethers, and mixture thereof, preferably dichloromethane, dichloroethane, toluene, ethyl acetate, or diethyl ether; most preferably dichloromethane. The organic base may be selected from the group consisting of triethylamine, diisopropylethylamine, N-methylmorpholine, pyridine, lutidine, and picoline, most preferably triethylamine.

The active ester or mixed anhydride is preferably formed at a temperature of about −20° C. to about 25° C. Most preferably, the temperature is about −10° C. to about 5° C. The obtained reaction mixture is treated with ammonia or an ammonia-generating reagent to produce compound of formula XIII.

(j) Reduction of compound of formula XIII with borane, or with sodium borohydride in presence of boron-trifluoride diethyl ether complex in tetrahydrofuran, or the like, at about −20° C. to 10° C., and contacting the resulting amine with a suitable acid HY in an organic solvent to produce a salt of formula XIV.

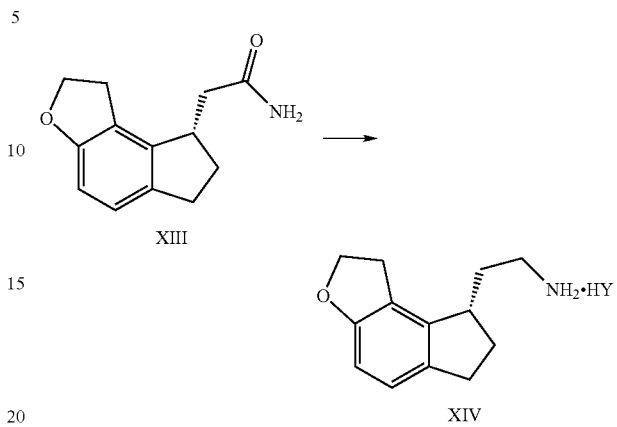

The acid HY preferably forms a pharmaceutically acceptable salt, including but not limited to sulphate, nitrate, phosphate, perchlorate, borate, hydrohalide, acetate, trifluoroacetate, tartrate, maleate, citrate, fumarate, succinate, palmoate, methanesulphonate, benzoate, salicylate, benzenesulfonate, ascorbate, glycerophosphate, and ketoglutarate.

(k) Reacting compound of formula XIV with propionyl chloride in presence of a base in a suitable organic solvent, to form non-electrostatic crystalline Form A of ramelteon.

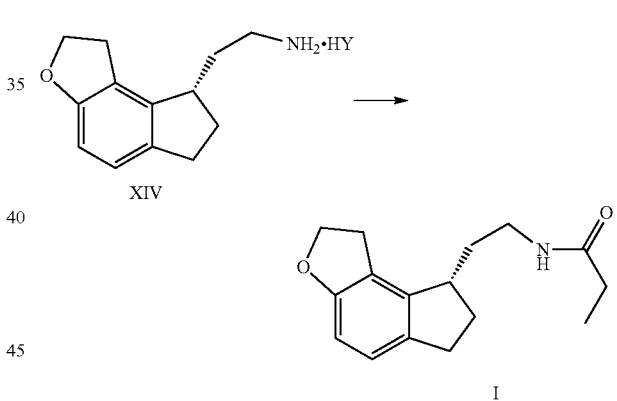

Suitable organic solvents include, but are not limited to, halogenated hydrocarbons, C$_6$ to C$_{14}$ aromatic hydrocarbons, C$_2$ to C$_7$ esters, C$_4$ to C$_7$ ethers, cyclic ethers, and mixture thereof, preferably dichloromethane, dichloroethane, toluene, ethyl acetate, or diethyl ether; most preferably dichloromethane. The base may be selected from the group consisting of inorganic bases such as sodium carbonate, sodium bicarbonate, potassium carbonate, potassium bicarbonate, and sodium hydroxide, or organic bases such as triethylamine, diisopropylethylamine, N-methylmorpholine, pyridine, lutidine, and picoline, most preferably triethylamine.

Compounds VII A, B and VIII A and B may be used as reference marker or standards to determine amount/and or location of compounds VII, VIII, ramelteon or other intermediates and impurities.

A compound in a relatively pure state can be used as a "reference standard" (a "reference marker" is similar to a reference standard but it is used for qualitative analysis) to quantify the amount of the compound in an unknown mixture.

When the compound is used as an "external standard," a solution of a known concentration of the compound is analyzed by the same technique as the unknown mixture. (Strobel p. 924, Snyder p. 549) (Snyder, L. R.; Kirkland, J. J. *Introduction to Modern Liquid Chromatography*, 2nd ed. (John Wiley & Sons: New York 1979)). The amount of the compound in the mixture can be determined by comparing the magnitude of the detector response. See also U.S. Pat. No. 6,333,198, incorporated herein by reference.

The reference standard compound also can be used to quantify the amount of another compound in the mixture if the "response factor," which compensates for differences in the sensitivity of the detector to the two compounds, has been predetermined. (Strobel p. 894). For this purpose, the reference standard compound may be added directly to the mixture, in which case it is called an "internal standard." (Strobel p. 925, Snyder p. 552).

The reference standard compound can even be used as an internal standard when the unknown mixture contains some of the reference standard compound by using a technique called "standard addition," wherein at least two samples are prepared by adding known and differing amounts of the internal standard. (Strobel pp. 391-393, Snyder pp. 571, 572). The proportion of detector response due to the reference standard compound that is originally in the mixture can be determined by extrapolation of a plot of detector response versus the amount of the reference standard compound that was added to each of the samples to zero. (e.g. Strobel, FIG. 11.4 p. 392).

In all of the embodiments described above, R and R' can be a $C_1$-$C_4$ alkyl, preferably methyl or ethyl.

EXAMPLES

Powder XRD (X-Ray Diffraction)

ARL X-ray powder diffractometer model X'TRA-030, Peltier detector, round standard aluminum sample holder with round zero background quartz plate [or silicon plate in the case of Form XIV] was used. The cathode is CuKa radiation, $\lambda$=1.5418 Å. Scanning parameters: Range: 2-40 deg. 2, continuous Scan, Rate: 3 deg/min. The accuracy of peak positions is defined as +/–0.2 degrees due to experimental differences like instrumentations, and sample preparations.
Chiral HPLC Method Conditions:
Column: Chiral PAK ADH (250×4.6) mm, 5μ
Mobile Phase: n-Heptane:Ethanol (95:5)
Diluent: n-heptane:Ethanol (50:50)
UV: 288 min
Run time: 30 min
Inj. Vol: 10 μL
Flow: 0.8 ml/min
Column oven: 15° C.
Sample Preparation: 500 ppm
HPLC Method Conditions for Chromatographic Purity:
Column: Xterra RP8, 3.5μ, 150×4.6 mm, Waters, P/N: 186000443 or equivalent.
Flow: 1.5 ml/min
Injection volume: 10 μl
Detector: 217 nm
Column Temperature: 30° C.
Equilibrium time: 10 minutes
Diluent: Acetonitrile Example 1

Synthesis of 2,3-dihydrobenzofuran-5-carboxaldehyde

Phosphorous oxychloride (255.58 g, 1.666 mol) was slowly added to a solution of DMF (355.0 ml) and 2,3-dihydrobenzofuran (100 g, 0.833 mol) maintaining the temperature 80-85° C. The reaction mixture was stirred for 4-5 hr and the reaction progress monitored by HPLC. The reaction mixture was then poured into ice water and extracted with toluene (2000 ml). The organic layer was washed with 5% sodium bicarbonate solution (500 ml) and then 10% brine solution (500 ml). The organic layer was distilled off under vacuum at 50-60° C. A liquid product was isolated. Yield: 85-90%, Purity: 90-92%

Example 2

Synthesis of Intermediate IV

A mixture of 2,3-dihydrobenzofuran-5-carbaldehyde (100.0 g, 0.6756 mol) and Malonic acid (175.67 g, 1.6891 mol) in pyridine (200 ml) containing piperidine (11.5 g, 0.135 mol) and acetic acid (4.05 g, 0.0676 mol) was heated at 100° C. for 4-5 hr. The reaction progress was checked by TLC and HPLC monitoring. The cooled reaction mixture was poured into aqueous HCl and stirred for 2-3 hr at room temperature. The solid mass was isolated by filtration and dried under the vacuum at 60-70° C. Yield: 92-95%, Purity: 95%

Example 3

Synthesis of Intermediate V

A solution of compound of formula IV (100 g, 0.526 mol) in methanol (1400 ml) and water (100 ml) was subjected to hydrogenation in the presence of 10% palladium on carbon (10 g) in a hydrogen atmosphere at room temperature for 1-2 hr. The reaction was monitored by HPLC. The reaction mixture was distilled off under vacuum at 60-70° C. until no additional solvent distilled off. Water was added dropwise, and the solid materials isolated and dried under vacuum at 60-70° C. Yield: 95% Purity 94-96%.

Example 4

Synthesis of Intermediate V

A solution of compound of formula IV (100 g, 0.5263 mol) in water (1000 ml), sodium hydroxide (42.0 g, 1.0526 mol) and ammonium formate (32.0 g, 0.5263 mol) subjected to hydrogenation in the presence of 10% palladium on carbon (10 g) in a hydrogen atmosphere at room temperature for 5-6 hr. The reaction was monitored by HPLC. The reaction mixture was filtered, and acidified with dilute HCl. The precipitated product was filtered off and dried under vacuum at 60-70° C. to afford the title compound. Yield: 95%, Purity: 94-96%.

Example 5

Synthesis of Intermediate VI

The compound of formula V (100 g, 0.521 mol) and sodium acetate (42.71 g, 0.5208 mol) were stirred in acetic acid (500.0 ml). The reaction mixture cooled at 0-5° C. and bromine (416.64 g, 2.604 mol) was added dropwise, maintaining the temperature at 0-5° C. The reaction mixture was heated 40-45° C. for 2-3 hr, while monitoring the reaction progress by HPLC. 15% Sodium bisulfite solution (1100 ml) was added dropwise, maintaining the temperature, and the solids were isolated by filtration and dried. Yield: 50-60%, Purity 92-95%.

Example 6

Synthesis of Intermediate VII

A mixture of compound of formula VI (100.0 g, 0.2857 mol) in o-dichlorobenzene (450 mol) and DMF (1.0 ml) was treated with thionyl chloride (44.2 g, 0.3714 mol) at room temperature and stirred for 1-2 hr. The reaction progress was checked by TLC. The reaction mixture was cooled to 0-5° C. and aluminum chloride (42.0 g, 0.314 mol) was added in portions at 0-5° C. The reaction mixture was stirred for 1-2 hr., then poured into methanol (1500 ml) with stirring. Solids were isolated by filtration and washed with 5% sodium bicarbonate solution and water, and dried under vacuum at 50-60° C.

Yield: 85-92%, Purity: 90-95%
For Impurity VII A:
   $H^1$NMR:
   2.674-2.708, 2H, m; 3.075-3.104 2H, t; 3.562-3.607, 2H, t; 4.746-4.791, 2H, t; 7.429, 1H, s
   $C^{13}$ NMR:
   25.16, 29.35, 37.03, 72.77, 110.26, 124.68, 128.76, 132.75, 148.05. 157.47, 206.36
For Impurity VII B:
   $H^1$NMR:
   2.740-2.769, 2H, m; 2.488-3.017, 2H, t; 3.363-3.406, 2H, t; 4.725-4.769, 2H, t; 7.196 1H, s
   $C^{13}$ NMR:
   24.35, 30.73, 37.88, 71.87, 98.34, 121.44, 133.87, 136.12, 151.37, 157.75, 203.74

Example 7

Synthesis of Intermediate II

The compound of formula VII (100.0 g, 0.3012 mol), sodium acetate (61.75 g, 0.753 mol), and 10% Pd/C (10.0 g) in methanol (3500 ml) were stirred under a hydrogen atmosphere (2-3 kg/cm²). The reaction progress was monitored by HPLC. The reaction mixture was filtered through a filter aid (CELITE HYFLO™), and the methanol was removed under vacuum at 50-60° C. The solid product was isolated by filtgration and dried under vacuum at 50-60° C. Yield 80-85% Purity 95-96%.

Example 8

Synthesis of Intermediate VIII

The compound of formula VII (100.0 g, 0.3012 mol), sodium acetate (61.75 g, 0.753 mol), and 10% Pd/C (10.0 g) in acetic acid (1000 ml) were stirred under a hydrogen atmosphere (2-3 kg/cm²). The reaction progress was monitored by HPLC. The reaction mixture was filtered through a filter aid (CELITE HYFLO™), and the acetic acid was removed under vacuum at 50-60° C. The solid product was isolated by filtration and dried under vacuum at 50-60° C.

Yield: 85-90% Purity: 96-97%.
For Impurity VIII A:
   $H^1$NMR:
   2.01-2.11 2H t; 2.756-3.058 HH m; 3.101-3.340 2H t; 4.500-4.542 2H t; 6.562-6.582 1H d; 6.929-6.949 1H d
   $C^{13}$ NMR:
   25.92, 28.72, 31.36, 32.11, 71.21, 106.70, 122.55, 122.92, 136.29, 140.86, 158.91

For Impurity VIII B:
   $H^1$NMR:
   1.87-1.93, 1H, m; 2.12-2.13, 1H, d; 2.40-2.48, 1H, m; 2.65-2.73, 1H, m; 2.89-2.97, 1H, m; 3.07-3.15, 1H, m; 3.23-3.32, 1H, m; 4.49-4.54, 2H, m; 5.15-5.18, 1H, t; 6.64-6.66, 1H, d; 6.92-6.94 1H, d)
   $C^{13}$ NMR:
Purification of Intermediate VIII:
   Crude compound of formula VIII (100 g) was heated to reflux in methanol (1500 ml) to produce a clear solution. This clear solution was decolorized by charcoal treatment with stirring at reflux temperature. The reaction mixture was filtered while hot through a filter aid (CELITE HYFLO™), and the filtrate was concentrated and then cooled to 10-15° C. and stirred for 1-2 hr. The product was collected by filtration, washed with cold methanol, and dried under reduced pressure at 50-60° C. Yield: 80-85%, Purity: 99.2-99.8%.

Example 9

Synthesis of Intermediate X

A 60% suspension of sodium hydride in mineral oil (34.4 g, 1.43 mol) was added to dry toluene (3000 ml) under a nitrogen atmosphere, cooled, and stirred at 0-5° C. for 15-20 minutes. Triethyl phosphonoacetate (257.1 g, 1.148 mol) was added dropwise at 0-5° C. and stirred for 2 hr at room temperature. Compound VIII (100.0 g, 0.5740 mol) was added, and the reaction mixture was heated to 90-100° C. and stirred under a nitrogen atmosphere for 15-18 hr. The reaction was monitored by HPLC. After completion of the reaction, the mixture was cooled and water was added slowly with stirring. The organic layer was separated, washed with brine, and concentrated under vacuum at 50-60° C. to leave crude product. Yield: 80-85%, Purity: 92-95%.

Example 10

Synthesis of Intermediate XI Via intermediate Xa

The compound of formula X (100 g, 0.4098 mol) and 10% Pd/C (10.0 g) in methanol (2500 ml) and water (500 ml) were stirred under a hydrogen atmosphere (2-3 kg/cm²) at room temperature for 2-3 hr. The reaction mixture was filtered, sodium hydroxide (53 g, 1.4 mol) was added, and the reaction mixture was stirred for 2-3 hr at room temperature to effect hydrolysis. The methanol was distilled of under vacuum, water was added, and the mixture was acidified by dropwise addition hydrochloric acid with cooling. The resulting recipitate was isolated by filtration and dried under vacuum at 60° C. Yield: 90-95%, Purity: 95-98%.

Example 11

Synthesis of (R)-XII and Intermediate (S)-XII

Purification of R-Isomer Using (S)-1-Phenylethylamine:
   (S)-1-Phenylethylamine (55.5 g, 1.0 mol) was added dropwise to a solution of compound XI (100 g, 1.0 mol) in isopropyl alcohol (1500 ml) and water (1000 ml) at 60-65° C., and stirred for 30-45 minutes. The mixture was gradually cooled to 5-10° C., and the phenethylamine salt XIIa (R-isomer) was collected by filtration and dried under vacuum at 50-60° C. Yield: 64-66%, Chiral Purity: 88-92%.
   The above salt was dissolved in water and acidified to pH 2.0 by dropwise addition of concentrated hydrochloric acid.

The precipitated free acid (R)-XII was collected and dried under vacuum at 50-55° C. Yield: 88-95%, Purity: 99.0-99.5%.

Purification of S-Isomer:

The filtrate from the above preparation, containing the S-isomer of salt XIIa, was concentrated, and the residue was dissolved in acetone:water (15:5 ratio) with heating, stirred for 30-40 minutes, and then cooled gradually to 10° C. The salt (S)-XII was collected by filtration. After two to three further recrystallizations from acetone:water (15:5 ratio), the S-salt was isolated by filtration and dried under vacuum at 50-55° C. Yield: 50-60%, Chiral Purity: 99.10% (S-isomer).

The above salt was dissolved in water and acidified to pH 2.0, and the precipitated free acid (S)-XII was collected and dried as described above for the (R)-isomer. Yield: 90-95%, Chiral Purity: 99.7-99.99% (S-isomer), Chemical Purity: 99.9 Specific optical rotation $[\alpha]^{20}_D$: +76.98 (S-isomer), 1.0% in chloroform.

Purification of S-Isomer Using (R)-1-Phenylethylamine:

(R)-1-Phenylethylamine (55.5 g, 1.0 mol) was added dropwise to a solution of compound XI (100 g, 1.0 mol) in acetone (4000 ml) at 60-65° C., and stirred for 30-45 minutes. The mixture was gradually cooled to 10° C., and the phenethylamine salt XIIa (S-isomer) was collected by filtration and dried under vacuum at 50-60° C. Yield: 70-80 g, Chiral Purity: 88-92% (S-isomer). The salt was recrystallized two or three times from acetone, and then isolated and dried under vacuum at 50-55° C. Yield: 50-60%, Chiral Purity: 99.10% (S-isomer)

Acidification as above, and drying the free acid under vacuum at 50-55° C. provided the free acid (S)-XII. Yield: 90-95%, Chiral Purity: 99.99% (S-isomer), Chemical Purity 99.9%.

Specific optical rotation $[\alpha]^{20}_D$: +76.980 (S-isomer), 1.0% in chloroform.

Purification of R-Isomer:

The filtrate from the above preparation, containing the R-isomer of salt XIIa, was concentrated, and the salt collected by filtration. Yield: 75-80%, Chiral Purity: 82-85%.

Example 12

Synthesis of Intermediate XIII

Method A1:

A solution of compound of formula (S)-XII (100.0 g, 0.4587 mol) and thionyl chloride (300 ml) was stirred for 3 hr at room temperature, checking reaction progress by TLC. Excess thionyl chloride was distilled off, dichloromethane was added, and again distillation was performed to remove traces of thionyl chloride. Ammonia gas was passed into a solution of the acid chloride in dichloromethane until a quenched sample tested alkaline. The precipitated product was filtered off and washed it with water and 5% bicarbonate solution. Yield: 85-90%, Purity: 95-98%.

Method A2:

A solution of acid chloride solution in dichloromethane, prepared as above, was added dropwise with stirring to 30-35% ammonia solution (500 ml). The precipitated product was filtered off and washed it with water and 5% bicarbonate solution. Yield: 85-90%, Purity: 93-96%.

Method B:

To a solution of the compound of formula XII (10.0 g, 0.045 mole) in dichloromethane (100 ml) and triethylamine (5.55 g, 0.055 mole), cooled to between −10° C. and 0° C., a solution of ethyl chloroformate (5.57 g, 0.0527 mole) in dichloromethane (10 ml) was added dropwise with stirring. Stirring was continued for 1 to 2 hr at −10° C. to 0° C., until TLC indicated that the formation of mixed anhydride was complete. The reaction mixture was added dropwise to a solution of ammonia in dichloromethane at −10° C. to 0° C., and the mixture was stirred for 30-45 min. Dichloromethane was removed under vacuum and the product was treated with 5% sodium bicarbonate solution (50 ml) with stirring. The compound of formula XIII was collected by filtration and dried under reduced pressure at 50-60° C. Yield: 80-95%, Purity: 97-99%.

Purification of Intermediate XIII:

A solution of compound XIII (100 g) in isopropanol (3000 ml), prepared by Method B above, was heated to produce a clear solution, and stirred for 30-35 minutes. The solution was decolorized with charcoal, filtered, and concentrated to 2000 ml, and then cooled to 15-20° C. The precipitated product was filtered off and washed with cold isopropanol and dried. Yield: 80-85%, Purity: 98-99%. Recrystallization from ethanol and acetonitrile was carried out with comparable results.

Example 13

Synthesis of Intermediate XIV (Y=chloride)

Method A:

Sodium borohydride (74.2 g, 1.96 mol) was added to a stirred solution of $BF_3$ etherate (247.8 ml) in THF (1800 ml) at −10° C. The reaction mixture was stirred for 1-2 hr at room temperature. The mixture was then cooled to 0° C. and compound XIII (100 g, 0.4608 mol) was added, and the reaction mixture was stirred at room temperature for 15-24 hr. Reaction progress was monitored by TLC and HPLC. THF was removed under vacuum at 40-50° C., the residue was diluted with ethyl acetate, and an excess of 1N HCl was added to the mixture. Ethyl acetate was removed under vacuum, and the remaining mixture was stirred for 30-40 minute at 50° C. The residue was then treated with isopropyl ether and the solids were filtered off and washed with acetone. Yield: 50-60 g, Purity 92-95%.

Example 14

Synthesis of Intermediate XIV (Y=oxalate)

Compound of formula XIII (100 g, 0.4608 mol) was reduced as in Example 13 above. The reaction mixture was quenched with 3600 ml water and 200 ml conc. hydrochloric acid. THF was removed under vacuum at 40-50° C., and the reaction mixture was diluted with toluene and basified with NaOH to pH 9-10. The organic layer was separated and washed with brine and sodium carbonate solution. The organic layer was concentrated in vacuum, a solution of oxalic acid in methanol was added, and the mixture was cooled to 0-5° C. The precipitated solid was filtered off, washed and dried under vacuum at 50-55° C. Yield: 80-85%, Purity: 96-98%.

Example 15

Synthesis of Ramelteon

A mixture of a compound of formula XIV (Y=Cl⁻) (100 g, 0.4175 mol) in THF (250 ml) and water (350 ml) was stirred at room temperature as 30% sodium hydroxide solution (10.0 ml) was added. Propionyl chloride (68.74 g 0.7432 mol) was added dropwise, and the mixture was stirred for 2-3 hr, monitoring by TLC and HPLC. The THF was removed in vacuum and the residue extracted into ethyl acetate. The ethyl acetate solution was washed with brine and concentrated in vacuum. The product ramelteon was recrystallized from ethanol. Yield: 50-60 g, Purity 97-99%.

Example 16

Synthesis of Ramelteon

Compound of formula XIV (Y=oxalate) (100 g, 0.376 mol) was stirred with sodium carbonate (1120 g, 1.1277 mol), water (600 ml), and dichloromethane (1000 ml) at room temperature. The mixture was cooled to 10 to −5° C. Propionyl chloride (51.02 g, 0.5638 mol) in dichloromethane was added dropwise with stirring, and the mixture was stirred for 1 hr, monitoring by TLC and HPLC. The organic layer was separated and washed with sodium bicarbonate and 10% brine. Concentration in vacuum provided ramelteon, which was recrystallized from ethanol. Yield: 92-96%, Purity: 99.5-99.9%.

Example 17

Synthesis of Ramelteon

A one-liter reactor was loaded with Compound XIV (Y=Cl$^-$) (17 g, 71 mmol) and water (85 ml). The resulting milky solution was stirred at room temperature for 5 min, followed by addition of toluene (340 ml) and 47% aqueous NaOH (13.31 ml, 235 mmol). The mixture was stirred at room temperature for 30 min. Propionyl chloride (13.08 g, 142 mmol) was added dropwise over a period of 40 min. HPLC monitoring indicated that reaction was complete at this point. The organic phase was separated, washed with aq. NaHCO$_3$ (85 ml) and brine (85 ml), and concentrated by distillation (45° C., 15 mmHg) to leave 80 ml of residue, which was cooled to room temperature. The resulting precipitate was collected by suction filtration and oven-dried (50° C., 24 h) to give ramelteon as a white solid. Yield: 82%.

Example 18

Crystallization of Ramelteon

A mixture of ramelteon in toluene (20V) was stirred under heating at 40-45° C. until the solid was fully dissolved to give clear solution. Then the obtained solution was concentrated by distillation of the toluene till the range of 4 to 10 volumes of the solvent in the reaction flask. The flask was allowed to reach room temperature and the white precipitate began to form. The solid was collected by suction filtration, dried in oven [35-50° C.; 16 h] to give the pure crystalline material in 73-86% yield; purity 99.53-99.79%.

Example 19

Electrostatic Charge Measurement

Equipment and Accessories
Electrical Shaker—Scientific Industries type Vortex-2 Genie (including specific holder for the shaking cans).
Electrostatic Charge Meter—Monroe Electronics type Nano-coulomb Meter 253 (Faraday Cup).
Metal shaking can, S.S. 316, 30×50_mm.
Plastic shaking can, Perspex, 30×50_mm.
Description of Test Procedure
Calibration of the Electrostatic Charge Meter, prior the test according to manufacturer's procedure.
6 sample cans were used for each batch.

The shaking can placed in flat dish, the sample cam was opened and the powder was manually poured into the shaking can.

The shaking can was hermetically closed by plastic cover and mounted in the holder.

The electrical shaker was operated for 90 seconds, at maximum rate.

Subsequent of the shaking period the shaking can was moved into the flat dish, the cover was removed and the powder was manually poured into a glass can within the Faraday-Cup. Some of the powder was transferred by gravitational pouring (90-99%), the rest was transferred by manually push using wooden spatula (with strict adherence to tender motion).

The Faraday-Cup was closed and the charge reading (in meter display) was recorded. The described test stages were equally conducted on the selected 6 samples of each batch, as follow: 3 powder samples were shaken in metal can, 3 powder samples were shaken in plastic can. All the samples were shaken in each can for the same time period of 90 seconds.
Results: Test in Plastic Can

| Batch No. | Sample | Reading nC | Calculated Charge Density, nC/gr | Average Charge Density of Batch, nC/gr |
|---|---|---|---|---|
| Ethyl Acetate | 1 | −20.2 | 10.1 | 10.82 |
|  | 2 | −28.1 | 14.05 |  |
|  | 3 | −16.6 | 8.3 |  |
| Toluene | 1 | −1.7 | 0.85 | 0.72 |
|  | 2 | −1.2 | 0.6 |  |
|  | 3 | −1.4 | 0.7 |  |

Test in Metal Can

| Batch No. | Sample No. | Reading nC | Calculated Charge Density, nC/gr | Average Charge Density of Batch, nC/gr |
|---|---|---|---|---|
| Ethyl Acetate | 1 | −17.6 | 8.8 | 9.63 |
|  | 2 | −20.2 | 10.1 |  |
|  | 3 | −20.0 | 10.0 |  |
| Toluene | 1 | −1.9 | 0.95 | 0.82 |
|  | 2 | −0.5 | 0.25 |  |
|  | 3 | −2.5 | 1.25 |  |

The average charge density of sample obtained from Ethyl acetate is about 15 times greater the average of sample obtained from Toluene in plastic can, and about 12 times greater in metal can.

1. Flowability
Instrument: FT4 Powder Rheometer (Freeman Technology Ltd).
Methodology: The blade was rotated and simultaneously moved axially into a powder sample whist axial force and rotational forces are measured.
The 25 mm blade and a 25 ml split borosilicate test vessel were used.
The Stability and Variable Flow Rate programs were run together by combining the two methods into one program (REP+VFR). The REP+VFR study is a combination of the seven conditioning and test cycles (blade tipspeed is 100 mm/s) at constant speed and the four conditioning and test cycles (blade tipspeed is 100, 70, 40 and 10 mm/s, respectively) with decreasing in blade speed.

Definitions of the Flow Parameters:
 Basic Flow Energy (BFE)=Energy Test 7, mJ
 Stability index (SI)=Energy test 7/Energy Test 1
Results

| Measurements | Sample from Ethylacetate | Sample from Toluene |
|---|---|---|
| BFE (mJ) | 181 | 92.5 |
| SI | 0.622 | 1.02 |

BFE—the sample from Toluene has a mush lower Basic Flow Energy than other. The lower BFE represents in most cases a powder with "good" flow properties and a high BFE, a powder that will flow poorly.
SI—the sample prepared from Toluene is not affected by being made to flow than other. Result of SI about 1 means no change between test 1 and test 7.

What is claimed is:
1. A compound having the structure:

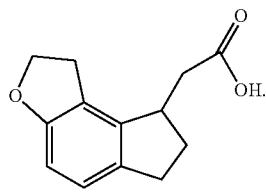

2. The compound of claim 1, wherein the compound exists as a racemic mixture.
3. The compound of claim 1 in enantiomeric form, having the structure:

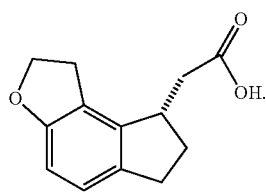

4. The compound of claim 1 in enantiomeric form, having the structure:

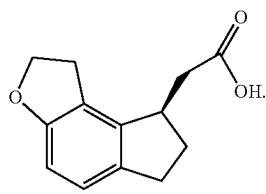

5. The compound of any one of claims 1-4, wherein the compound is isolated.
6. The compound of any one of claims 3 and 4, wherein the compound has a chiral purity of about 90% to about 100%, as measured by HPLC.
7. The compound of claim 1, wherein the compound has a chemical purity of about 90% to about 100%, as measured by HPLC.

8. The compound of claim 1, wherein the compound has chemical purity of about 90% to about 100% as measured by HPLC and a chiral purity of about 90% to about 100%.
9. A salt of a chiral amine having the following structure:

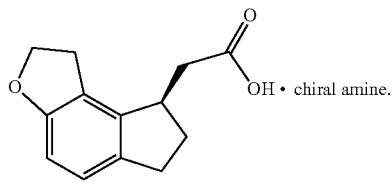

XIIa

10. A salt of a chiral amine having the following structure:

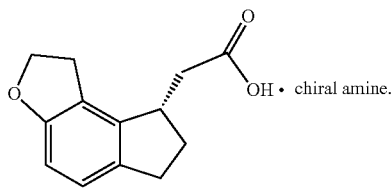

XIIa

11. The salt of any one of claims 9 or 10, wherein the amine has one of the following structures:

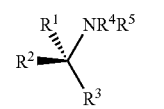

1

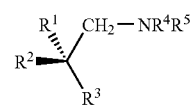

2 wherein $R^1$ through $R^5$ are independently H, $C_1$-$C_{10}$ alkyl, $C_6$-$C_{10}$ aryl, or $C_5$-$C_9$ heteroaryl, and $R^1$, $R^2$, and $R^3$ are all different from one another.

12. The salt of any one of claims 9 or 10, wherein the amine is selected from the group consisting of (R)-1-phenylethylamine, (S)-1-phenylethylamine, (R)-1-(4-methylphenyl)ethylamine, (S)-1-(4-methylphenyl)ethylamine, (R)-1-(2-methoxyphenyl)ethylamine, (S)-1-(2-methoxyphenyl)ethylamine, (R)-1-(3-methoxyphenyl)ethylamine, (S)-1-(3-methoxyphenyl)ethylamine, (R)-1-(4-methoxyphenyl)ethylamine, (S)-1-(4-methoxyphenyl)ethylamine, (R)-1-(4-chlorphenyl)ethylamine, (S)-1-(4-chlorphenyl)ethylamine, (R)-1-(3-chlorphenyl)ethylamine, (S)-1-(3-chlorphenyl)ethylamine, (R)-1-(3-bromophenyl)ethylamine, (S)-1-(3-bromophenyl)ethylamine, (R)-1-(4-bromophenyl)ethylamine, (S)-1-(4-bromophenyl)ethylamine, (R)-1-(4-fluorpheny)ethylamine, (S)-1-(4-fluorphenyl)ethylamine, (R)-1-(3,4-dimethoxyphenyl)ethylamine, (S)-1-(3,1-dimethoxyphenyl)ethylamine, (R)-1-(1-naphthyl)ethylamine, (S)-1-(1-naphthyl)ethylamine, (R)-1-aminotetralin, (S)-1-aminotetralin, (R)-1-aminoindane, (S)-1-aminoindane, (R)-1-(2-naphthyl)ethylamine, (S)-1-(2-naphthyl)ethylamine, (R)-3-methyl-2-butylamine, (S)-3-methyl-2-butylamine, (R)-2-hexylamine, (S)-2-hexylamine, (R)-2-heptylamine, (S)-2-heptylamine, (R)-2-octylamine, (S)-2- octylamine, (R)-2-nonylamine, (S)-2-nonylamine, (R)-3,3-dimethyl-2-aminobutane, (S)-3,3-dimethyl-2-aminobutane, (R)-1-cyclopropylethylamine, (S)-1-cyclopropylethylamine, (R)-1-cyclohexylethylamine, (S)-1-cyclohexylethylamine, (R)-1-phenylpropylamine, (S)-1-phenylpropylamine, (R)-1-phenylbutylamine, (S)-1-phenylbutylamine, (S)-1-methoxy-2-aminopropane, (1R-trans)-2-(phenylmethoxy)cyclopentylamine, (1S-trans)-2-(phenylmethoxy)cyclopentaneamine, (1R-trans)-2-(phenylmethoxy)cyclohexylamine, (1S-trans)-2-(phenylmethoxy)cyclohexylamine, (R)--N-benzyl-1-phenylethylamine, (S)—N-benzyl-1-phenylethylamine, (R,R)-bis-(1-phenylethyl)amine, (S,S)-bis-(1-phenylethyl)amine, (R)-1-phenylethylhydroxylamine, (S)-1-phenylethylhydroxylamine, (1R,2R)-ephedrine, (1S,2S)-ephedrine, (1R,2S)-ephedrine, and (1S,2R)-ephedrine.

13. The salt of claim 12, wherein the amine is (R)-1-phenylethylamine.

14. The salt of claim 12, wherein the amine is (S)-1-phenylethylamine.

15. A compound having the Formula X:

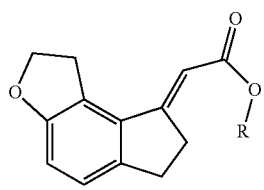

wherein R is selected from the group consisting of $C_1$ to $C_6$ straight or branched alkyl, $C_6$ to $C_{10}$ aryl, and $C_7$ to $C_{12}$ arylalkyl.

16. A compound having the Formula

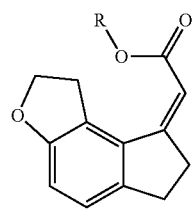

wherein R is selected from the group consisting of $C_1$ to $C_6$ straight or branched alkyl, $C_6$ to $C_{10}$ aryl, and $C_7$ to $C_{12}$ arylalkyl.

17. A mixture of compounds having structures

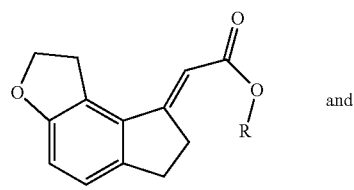

and

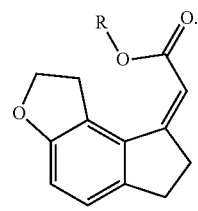

18. A compound having the Formula Xa:

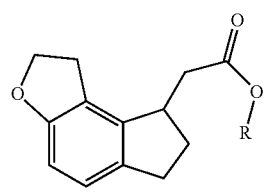

wherein R is selected from the group consisting of $C_1$ to $C_6$ straight or branched alkyl, $C_6$ to $C_{10}$ aryl, and $C_7$ to $C_{12}$ arylalkyl.

19. The compound of claim 18 in enantiomeric form having the structure:

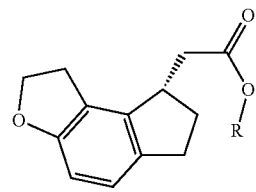

wherein R is selected from the group consisting of $C_1$ to $C_6$ straight or branched alkyl, $C_6$ to $C_{10}$ aryl, and $C_7$ to $C_{12}$ arylalkyl.

20. The compound of claim 19, wherein the compound has a chemical purity of more than about 90% to about 100%, as measured by HPLC.

21. A process for the preparation of the compound of formula IV comprising reacting the compound of formula II with malonic acid of formula III in the presence of a base and acetic acid to form compound IV:

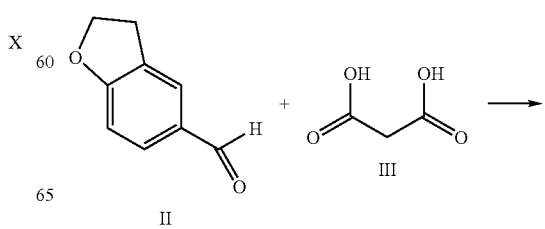

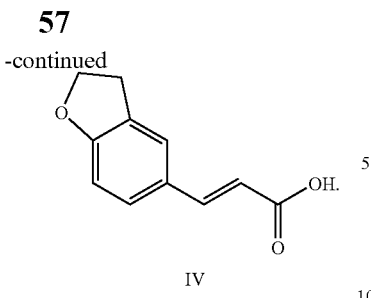

IV

22. A method for the preparation of ramelteon, which comprises:
(a) reacting the compound of formula II with malonic acid of formula III in the presence of a base to form compound IV

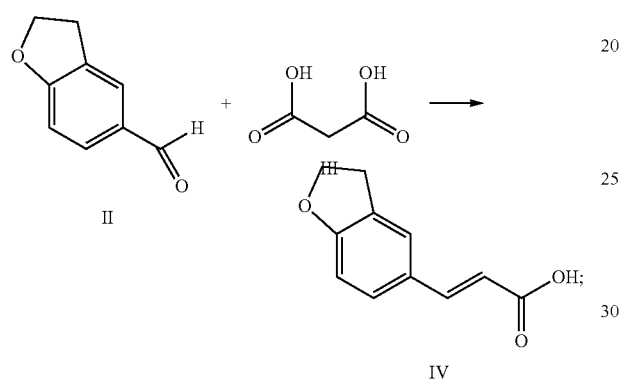

(b) reducing the compound of formula IV to obtain the compound of formula V

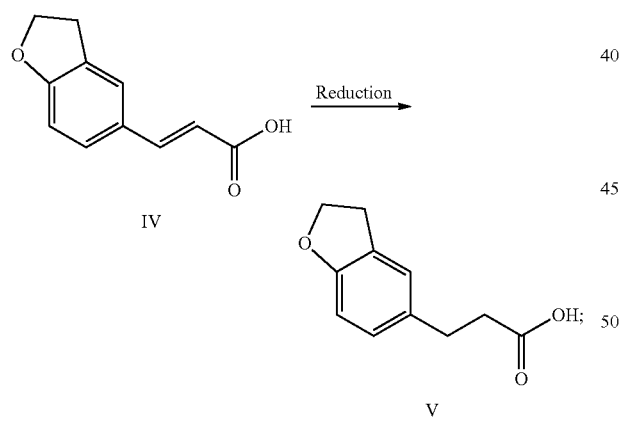

(c) contacting the compound of formula V with a halogenation agent to form the compound of formula VI

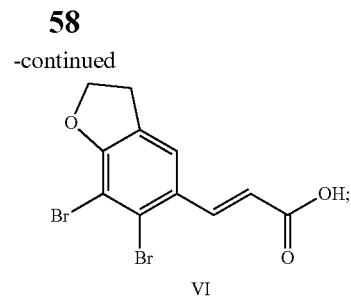

VI (d) cyclizing and reductively dehalogenating the compound of formula VI to produce the compound of formula VIII

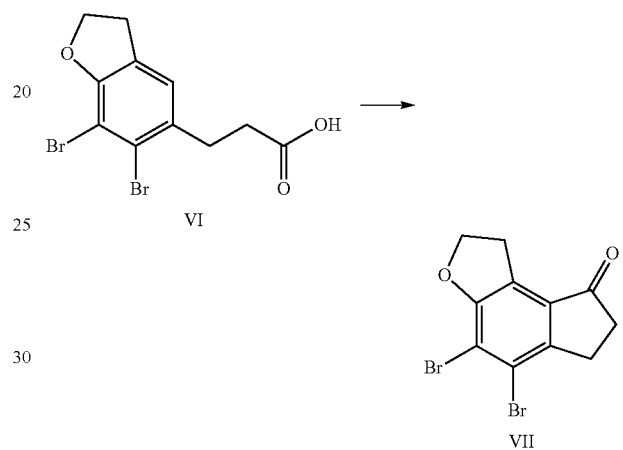

(e) contacting the compound of formula VIII with a compound of formula IX to produce a compound of formula X, wherein R and R' are independently phenyl, benzyl, or $C_1$-$C_8$ straight, cyclic or branched alkyl

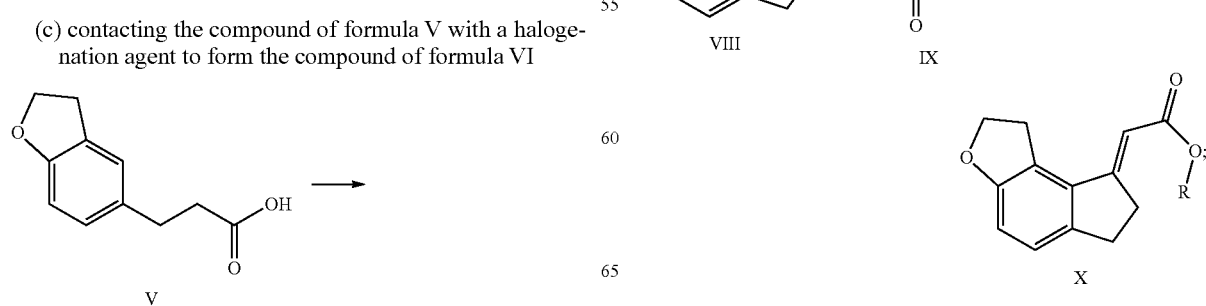

(f) hydrolyzing the compound of formula X, and reduction of the double bond, to obtain the compound of formula XI, wherein either reaction may precede the other

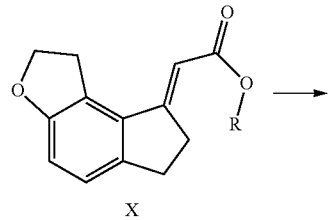

X

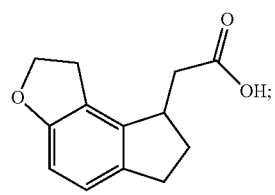

XI (g) resolving the compound of formula XI by contacting with an organic chiral amine to obtain the diastereomeric amine salts of formula XIIa, followed by isolation of a single diastereomer by crystallization and subsequent treatment with acid to form the compound of formula (S)-XII

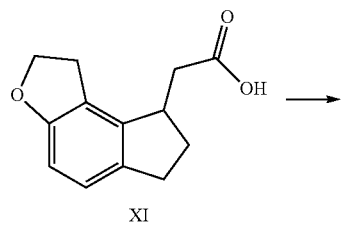

XI

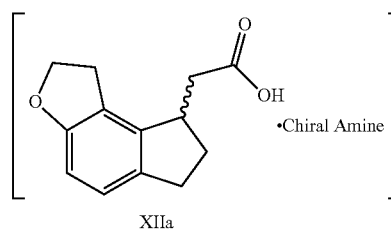

XIIa

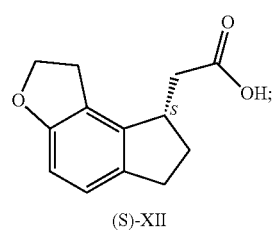

(S)-XII (h) amidating the compound of formula (S)-XII to produce the compound of formula XIII

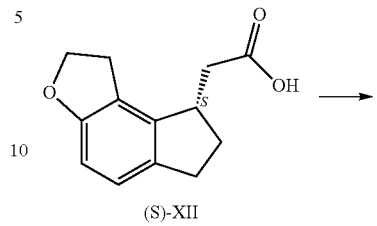

(S)-XII

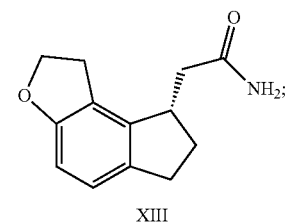

XIII (i) reducing the compound of formula XIII with an amide reducing agent, followed by formation of a salt of formulat XIV wherein Y is an organic or inorganic anion;

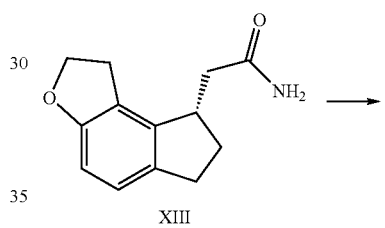

XIII

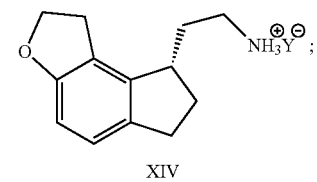

XIV and (j) acylation of the amino group of compound XIV to form ramelteon.

23. The process according to claim 22, wherein in step (a) the base is selected from the group consisting of alkali metal and alkaline earth carbonates and hydroxides; and primary, secondary, and tertiary amines.

24. The process according to any one of claims 22 or 23, wherein in step (b) the reduction is carried out with formate/Pd-C or $H_2$/Raney-Ni.

25. The process according to claim 22, wherein in step (c) the halogenation agent is bromine.

26. The process according to claim 22, wherein in step (f) the reduction is carried out with $H_2$/Pd-C or $H_2$/Raney-Ni.

27. The process according to claim 22, wherein in step (g) the chiral amine is selected from the group consisting of (R)-1-phenylethylamine, (S)-1-phenylethylamine, (R)-1-(4-methylphenyl)ethylamine, (S)-1-(4-methylphenyl)ethylamine, (R)-1-(2-methoxyphenyl)ethylamine, (S)-1-(2-methoxyphenyl)ethylamine, (R)-1-(3-methoxyphenyl)ethylamine, (S)-1-(3-methoxyphenyl)ethylamine, (R)-1-(4- methoxyphenyl)ethylamine, (S)-1-(4-methoxyphenyl)ethylamine, (R)-1-(4-chlorphenyl)ethylamine, (S)-1-(4-chlorphenyl)ethylamine, (R)-1-(3-chlorophenyl)ethylamine, (S)-1-(3-chlorophenyl)ethylamine, (R)-1-(3-bromophenyl)ethylamine, (S)-1-(3-bromophenyl)ethylamine, (R)-1-(4-bromophenyl)ethylamine, (S)-1-(4-bromophenyl)ethylamine, (R)-1-(4-fluorophenyl)ethylamine, (S)-1-(4-fluorophenyl)ethylamine, (R)-1-(3,1-dimethoxyphenyl)ethylamine, (S)-1-(3,1-dimethoxyphenyl)ethylamine, (R)-1-(1-naphthyl)ethylamine, (S)-1-(1-naphthyl)ethylamine, (R)-1-aminotetralin, (S)-1-aminotetralin, (R)-1-aminoindane, (S)-1-aminoindane, (R)-1-(2-naphthy)ethylamine, (S)-1-(2-naphthyl)ethylamine, (R)-3-methyl-2-butylamine, (S)-3-methyl-2-butylamine, (R)-2-hexylamine, (S)-2-hexylamine, (R)-2-heptylamine, (S)-2-heptylamine, (R)-2-octylamine, (S)-2-octylamine, (R)-2-nonylamine, (S)-2-nonylamine, (R)-3,3-dimethyl-2-aminobutane, (S)-3,3-dimethyl-2-aminobutane, (R)-1-cyclopropylethylamine, (S)-1-cyclopropylethylamine, (R)-1-cyclohexylethylamine, (S)-1-cyclohexylethylamine, (R)-1-phenylpropylamine, (S)-1-phenylpropylamine, (R)-1-phenylbutylamine, (S)-1-phenylbutylamine, (S)-1-methoxy-2-aminopropane, (1R-trans)-2-(phenylmethoxy)cyclopentylamine, (1S-trans)-2-(phenylmethoxy)cyclopentaneamine, (1R-trans)-2-(phenylmethoxy)cyclohexylamine, (1S-trans)-2-(phenylmethoxy)cyclohexylamine, (R)—N-benzyl-1-phenylethylamine, (S)—N-benzyl-1-phenylethylamine, (R,R)-bis-(1-phenylethyl)amine, (S,S)-bis-(1-phenylethyl)amine, (R)-1-phenylethylhydroxylamine, (S)-1-phenylethylhydroxylamine, (1R,2R) ephedrine, (1S,2S) ephedrine, (1R,2S) ephedrine, and (1S,2R) ephedrine.

28. A method for the preparation of ramelteon, which comprises the following steps:
(a) contacting the compound of formula VIII with a compound of formula IX to produce a compound of formula X, wherein R and R' are independently phenyl, benzyl, or $C_1$-$C_8$ straight, cyclic or branched alkyl (b) hydrolyzing the compound of formula X, and reduction of the double bond, to obtain the compound of formula XI, wherein either reaction may precede the other

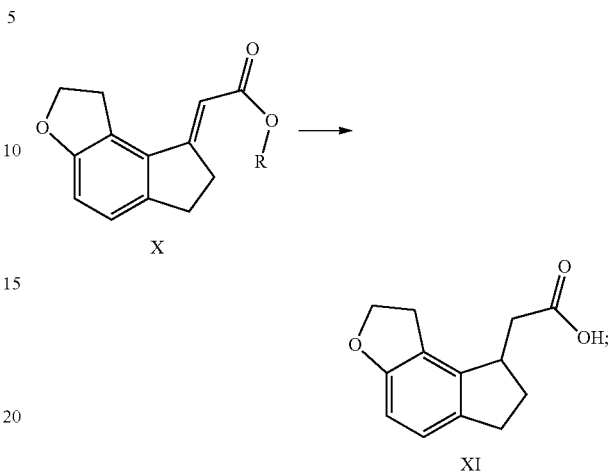

(c) resolving the compound of formula XI by contacting with an organic chiral amine to obtain the diastereomeric amine salts of formula XIIa, followed by isolation of a single diastereomer by crystallization and subsequent treatment with acid to form the compound of formula (S)-XII

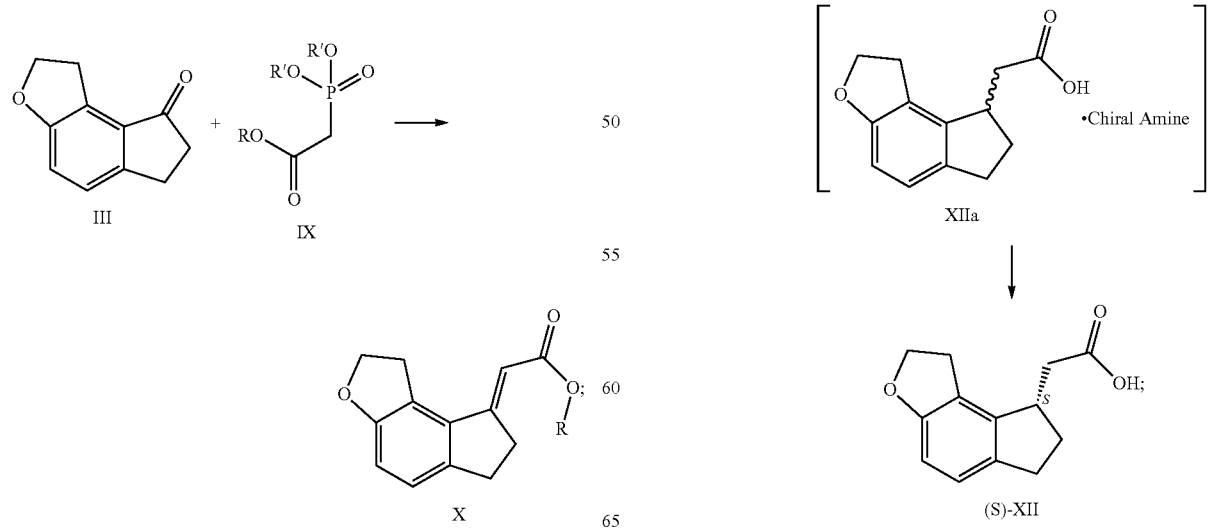

(d) amidating the compound of formula (S)-XII to produce the compound of formula XIII

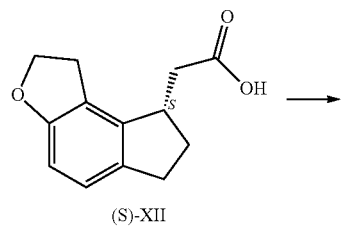

(S)-XII

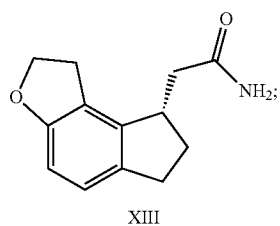

XIII (e) reducing the compound of formula XIII with an amide reducing agent, followed by formation of a salt of formula XIV wherein Y is an organic or inorganic anion;

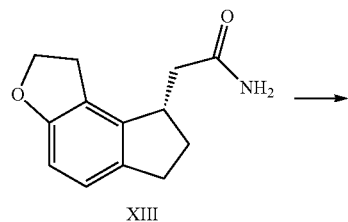

XIII

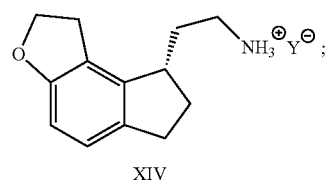

XIV and (f) acylation of the amino group of compound XIV to form ramelteon.

29. The method of claim 28, wherein the compound of structure VIII is prepared by a process comprising the following steps:

(a) contacting the compound of formula V with a halogenation agent to form the compound of formula VI

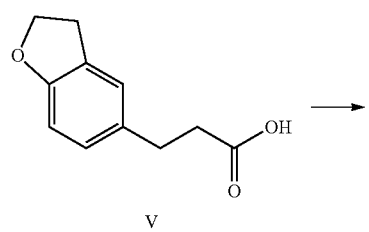

V

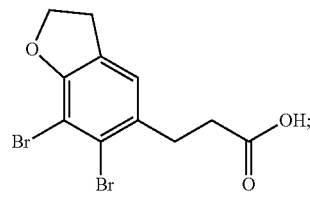

VI and (b) cyclizing and reductively dehalogenating the compound of formula VI

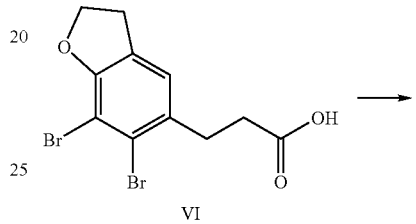

VI

VII

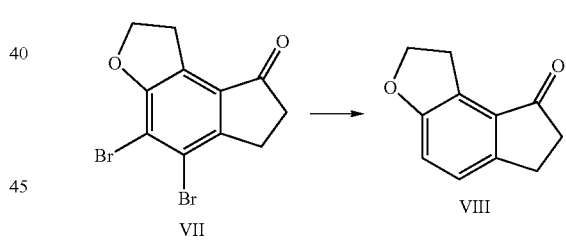

VII        VIII to produce the compound of formula VIII.

30. A method of preparing an intermediate in the synthesis of ramelteon comprising the following steps:

(a) contacting the compound of formula VIII with a compound of formula IX to produce a compound of formula X, wherein R and R' are independently phenyl, benzyl, or $C_1$-$C_8$ straight, cyclic or branched alkyl

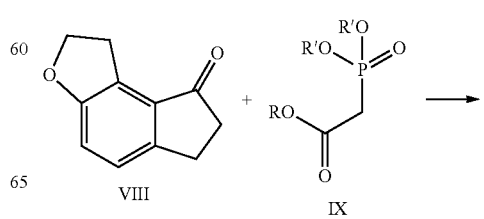

VIII        IX

-continued

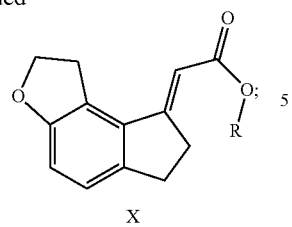

X (b) hydrolyzing the compound of formula X, and reduction of the double bond, to obtain the compound of formula XI, wherein either reaction may precede the other

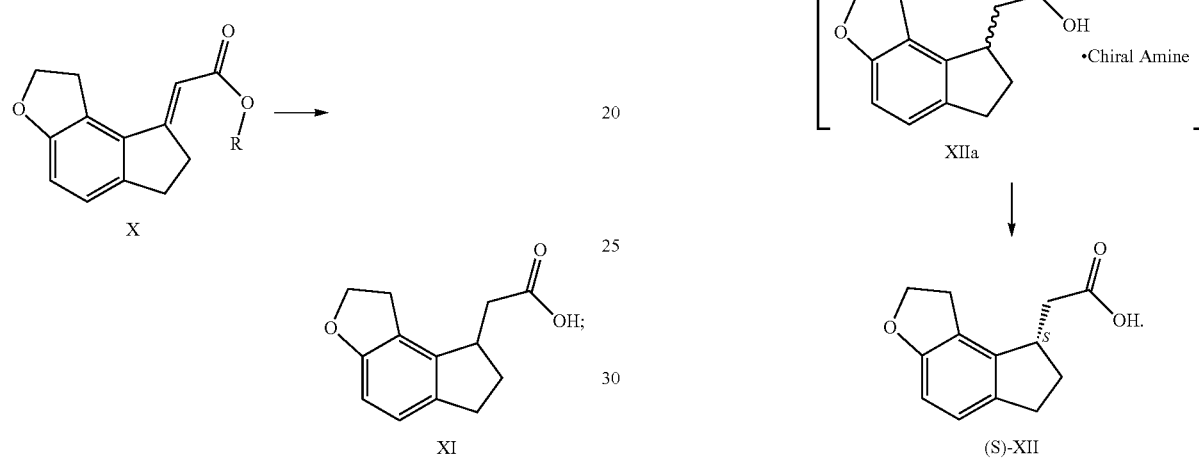

and (c) resolving the compound of formula XI by contacting with an organic chiral amine to obtain the diastereomeric amine salts of formula XIIa, followed by isolation of a single diastereomer by crystallization and subsequent treatment with acid to form the compound of formula (S)-XII

31. A method of isolating the compound of claim 5, comprising the step of recrystallizing a salt formed with (R)-1-phenylethylamine or (S)-1-phenylethylamine.

* * * * *